US009636511B2

(12) United States Patent
Carney et al.

(10) Patent No.: US 9,636,511 B2
(45) Date of Patent: May 2, 2017

(54) TISSUE CONDUCTION COMMUNICATION (TCC) TRANSMISSION

(71) Applicant: Medtronic, Inc., Minneapolis, MN (US)

(72) Inventors: James K. Carney, Roseville, MN (US); Joseph Ballis, Shoreview, MN (US); James D. Reinke, Maple Grove, MN (US); Can Cinbis, Salt Lake City, UT (US); Kevin P. Kuehn, Shoreview, MN (US); Mark A. Griebel, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 169 days.

(21) Appl. No.: 14/603,938

(22) Filed: Jan. 23, 2015

(65) Prior Publication Data

US 2016/0213939 A1    Jul. 28, 2016

(51) Int. Cl.
 *A61N 1/00*  (2006.01)
 *A61N 1/39*  (2006.01)
 *A61N 1/05*  (2006.01)

(52) U.S. Cl.
 CPC ......... *A61N 1/3956* (2013.01); *A61N 1/3962* (2013.01); *A61N 1/3975* (2013.01); *A61N 1/05* (2013.01)

(58) Field of Classification Search
 CPC .... A61N 1/36142; A61N 1/39; A61N 1/3925; A61N 1/3931; A61N 1/3981;
 (Continued)

(56) References Cited

U.S. PATENT DOCUMENTS 3,967,202 A    6/1976    Batz
4,987,897 A    1/1991    Funke
(Continued)

FOREIGN PATENT DOCUMENTS

EP    2441491 A1    4/2012
WO    2010042750 A2    4/2010
(Continued)

OTHER PUBLICATIONS (PCT/US2016/014501) PCT Notification of Transmittal of the International Search Report and the Written Opinion of the International Searching Authority, Mailed May 17, 2016, 10 pages.
(Continued)

*Primary Examiner* — Mallika D Fairchild

(57) ABSTRACT

An implantable cardioverter defibrillator (ICD) configured to transmit a tissue conduction communication (TCC) signal includes a TCC transmitter module configured to generate the TCC signal and transmit the TCC signal via a plurality of electrodes. The TCC signal comprises a biphasic signal having an amplitude and a frequency, wherein at least one of the amplitude and the frequency are configured to avoid stimulation of tissue of the patient. The TCC transmitter module comprises protection circuitry coupled between a current source and the plurality of electrodes, wherein the protection circuitry is configured to protect the signal generator from an external anti-tachyarrhythmia shock delivered to the patient.

20 Claims, 17 Drawing Sheets

(58) Field of Classification Search
CPC .. A61N 1/3956; A61N 1/3975; A61N 1/3962; A61N 1/05
See application file for complete search history.

(56) References Cited

U.S. PATENT DOCUMENTS

| | | | |
|---|---|---|---|
| 5,107,833 A | | 4/1992 | Barsness |
| 5,113,859 A | | 5/1992 | Funke |
| 5,117,824 A | | 6/1992 | Keimel et al. |
| 5,545,186 A | | 8/1996 | Olson et al. |
| 5,591,218 A | * | 1/1997 | Jacobson ............. A61N 1/3704 128/908 |
| 5,755,736 A | | 5/1998 | Gillberg et al. |
| 6,115,636 A | | 9/2000 | Ryan |
| 6,201,993 B1 | | 3/2001 | Kruse et al. |
| 6,788,973 B2 | | 9/2004 | Davis et al. |
| 6,847,298 B2 | | 1/2005 | Lunenburg et al. |
| 7,630,767 B1 | | 12/2009 | Poore et al. |
| 7,991,467 B2 | | 8/2011 | Markowitz et al. |
| 8,083,674 B2 | | 12/2011 | Such et al. |
| 8,258,962 B2 | | 9/2012 | Robertson et al. |
| 8,412,352 B2 | | 4/2013 | Griswold et al. |
| 8,457,742 B2 | | 6/2013 | Jacobson |
| 8,515,559 B2 | | 8/2013 | Roberts et al. |
| 8,540,633 B2 | | 9/2013 | Hafezi et al. |
| 8,543,190 B2 | | 9/2013 | Wasson et al. |
| 8,547,248 B2 | | 10/2013 | Zdeblick et al. |
| 8,744,572 B1 | | 6/2014 | Greenhut et al. |
| 8,798,205 B2 | | 8/2014 | Ecker et al. |
| 2006/0085041 A1 | | 4/2006 | Hastings et al. |
| 2006/0136004 A1 | | 6/2006 | Cowan et al. |
| 2007/0088394 A1 | | 4/2007 | Jacobson |
| 2008/0071328 A1 | | 3/2008 | Haubrich et al. |
| 2010/0114195 A1 | * | 5/2010 | Burnes ............. A61N 1/0504 607/4 |
| 2010/0198312 A1 | * | 8/2010 | Stevenson ............. A61N 1/05 607/63 |
| 2011/0160557 A1 | | 6/2011 | Cinbis et al. |
| 2011/0160801 A1 | | 6/2011 | Markowitz et al. |
| 2012/0081201 A1 | | 4/2012 | Norgaard et al. |
| 2012/0109236 A1 | | 5/2012 | Jacobson et al. |
| 2013/0116529 A1 | | 5/2013 | Min et al. |
| 2013/0211470 A1 | | 8/2013 | Benecke et al. |
| 2013/0253345 A1 | | 9/2013 | Griswold et al. |
| 2014/0277286 A1 | | 9/2014 | Cinbis |
| 2014/0379048 A1 | * | 12/2014 | Von Arx ............. A61N 1/362 607/60 |
| 2015/0174414 A1 | | 6/2015 | Stahmann et al. |
| 2015/0196756 A1 | | 7/2015 | Stahmann et al. |
| 2015/0360036 A1 | | 12/2015 | Kane et al. |
| 2016/0213937 A1 | | 7/2016 | Reinke et al. |

FOREIGN PATENT DOCUMENTS

| | | |
|---|---|---|
| WO | 2010051385 A1 | 5/2010 |
| WO | 2012057861 A1 | 5/2012 |
| WO | 2013080038 A2 | 6/2013 |

OTHER PUBLICATIONS

Wikipedia, "Radio Spectrum," https://en.wikipedia.org/wiki/Radio_spectrum, accessed Jul. 26, 2016, 11 pp.

* cited by examiner

TISSUE CONDUCTION COMMUNICATION (TCC) TRANSMISSION

TECHNICAL FIELD

The disclosure relates to medical devices and, more particularly, to communication between implantable medical devices.

BACKGROUND

A wide variety of implantable medical devices (IMDs) for delivering a therapy or monitoring a physiological condition have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Implantable cardioverter defibrillators, for example, may be used to deliver high energy defibrillation and/or cardioversion shocks to a patient's heart when atrial or ventricular tachyarrhythmia, e.g., tachycardia or fibrillation, is detected. An implantable cardioverter defibrillator (ICD) may detect a tachyarrhythmia based on an analysis of a cardiac electrogram sensed via electrodes, and may deliver anti-tachyarrhythmia shocks, e.g., defibrillation shocks and/or cardioversion shocks, via electrodes. An implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. Implantable cardiac pacemakers may also provide overdrive cardiac pacing, referred to as anti-tachycardia pacing (ATP), to suppress or convert detected tachyarrhythmias. Implanted cardiac pacemakers may sense a cardiac electrogram and deliver cardiac pacing pulses via electrodes. ICDs may also deliver ATP or other cardiac pacing, in some cases.

Some IMDs are coupled to one or more of the electrodes used to sense electrical physiological signals and deliver electrical stimulation via one or more leads, which allow the IMD housing to be positioned a desired distance from the target site for sensing or stimulation delivery. For example, a subcutaneously or sub-muscularly implanted housing of an ICD or implantable cardiac pacemaker may be coupled to endocardial electrodes via leads. Other ICDs, referred to as extravascular ICDs, are not coupled to any endocardial electrodes, and instead sense and deliver shocks via a plurality of electrodes, e.g., implanted subcutaneously or substernally, which may be provided by the housing of the subcutaneous ICD and/or coupled to the housing via one or more leads.

Leadless IMDs may also be used to deliver therapy to a patient, and/or sense physiological parameters of a patient. In some examples, a leadless IMD may include one or more electrodes on its outer housing to deliver therapeutic electrical stimulation to patient, and/or sense intrinsic electrical signals of patient. For example, a leadless pacing device (LPD) may be used to sense intrinsic depolarizations or other physiological parameters of the heart, and/or deliver therapeutic electrical stimulation to the heart. LPDs may be positioned within or outside of the heart and, in some examples, may be anchored to a wall of the heart via a fixation mechanism.

In some situations, two or more IMDs are implanted within a single patient. For example, as an alternative to an ICD with cardiac pacing capabilities coupled to endocardial electrodes via transvenous leads, it has been proposed to implant an extravascular ICD capable of delivering shocks, and a separate LPD capable of providing cardiac pacing. In some situations, it may be desirable for the two or more IMDs to be able to communicate with each other, e.g., to coordinate, or cooperatively provide, sensing and/or therapy delivery. For example, it may be desirable to allow an extravascular ICD and LPD to communicate to coordinate delivery of ATP and shocks in response to a tachyarrhythmia detected by one or both of the IMDs. Although some IMDs communicate with external devices, e.g., programming devices, using radio-frequency (RF) telemetry, it has also been proposed to use tissue conduction communication (TCC) for communication between an IMD and an external device, or between an IMD and another IMD.

SUMMARY

Generally, this disclosure describes various techniques for facilitating transmission of tissue conduction communication (TCC) signals by an implantable cardioverter defibrillator (ICD), such as an extravascular ICD. More particularly, this disclosure describes ICDs that include a signal generator that comprises both a shock module configured to generate a relatively higher-amplitude anti-tachyarrhythmia shock, e.g., defibrillation and/or cardioversion shock, for delivery to the patient, and a TCC transmitter module configured to generate a relatively lower-amplitude TCC signal for transmission via the patient. The TCC signal may comprise a biphasic signal having an amplitude and/or a frequency configured to avoid stimulation of tissue of the patient.

Both the anti-tachyarrhythmia shock and the TCC signal may be delivered via the same electrodes, such as a coil electrode and a housing electrode of the ICD. When the ICD delivers a defibrillation or cardioversion shock, several hundred volts are developed between the electrodes. In another case, an external defibrillator may be applied across the chest of the patient having an extravascular ICD, which may result in voltages greater than 2000 volts between the electrodes. ICDs are designed with components that protect the ICD circuitry from these high voltages. The TCC transmitter module may compromise the high-voltage stand-off of the ICD unless the module includes protection circuitry that can withstand the high voltage of a shock from the ICD or from an external defibrillator.

In some examples, the TCC signal is capacitively coupled to the electrodes. In such examples, the protection circuitry includes capacitors respectively coupled to each of the electrodes. In some examples, the one or more of the capacitors are coupled to one or more inductors, and the protection circuitry comprises one or more LC circuits, which may also be referred to as resonant circuits, tank circuits, or tuned circuits. The one or more LC circuits may be tuned to provide a pass-band that includes the frequency of the TCC signal. In some examples, the TCC signal is delivered to the electrodes by high-voltage switches, and the protection circuitry comprises such switches. In general, TCC transmitter modules according to this disclosure may be both able to generate a relatively low amplitude TCC signal at a desired frequency for transmission via defibrillation electrodes, and include protection circuitry to protect circuitry within the ICD from relatively high amplitude anti-tachyarrhythmia shocks. Additionally, in some examples, the ICD may include an induction module configured to generate a signal that induces fibrillation of the heart of a patient for delivery via the electrodes, and the TCC transmitter module may use circuitry from the shock module and/or the induction module to generate a TCC signal, which may advantageously facilitate a relatively smaller number or volume of circuit components, and accordingly size, of the ICD.

In one example, the disclosure describes an implantable cardioverter defibrillator (ICD) configured to transmit a tissue conduction communication (TCC) signal. The ICD comprises a housing, and a signal generator within the housing. The signal generator comprises a shock module coupled to a plurality of electrodes, wherein the shock module is configured to generate an anti-tachyarrhythmia shock and deliver the anti-tachyarrhythmia shock to a patient via the plurality of electrodes. The signal generator further comprises a TCC transmitter module coupled to the plurality of electrodes, wherein the TCC transmitter module is configured to generate the TCC signal and transmit the TCC signal via the plurality of electrodes, wherein the TCC signal comprises a biphasic signal having an amplitude and a frequency, and wherein at least one of the amplitude or the frequency is configured to avoid stimulation of tissue of the patient by the TCC signal. The TCC transmitter module comprises a power source configured to deliver current having the amplitude to the plurality of electrodes, polarity switching circuitry coupled to the power source, wherein the polarity switching circuitry is configured to switch the polarity of the current at the frequency, and protection circuitry coupled between the power source and the plurality of electrodes, wherein the protection circuitry is configured to protect the TCC transmitter module and other circuitry within the housing of the ICD from an anti-tachyarrhythmia shock delivered to the patient by the shock module or an external device.

In another example, the disclosure describes an extravascular implantable cardioverter defibrillator (ICD) configured to transmit a tissue conduction communication (TCC) signal. The extravascular ICD comprises a housing configured for extravascular implantation within a patient, wherein the housing comprises a housing electrode, and a signal generator within the housing. The signal generator comprises a shock module coupled to the housing electrode and a coil electrode, wherein the coil electrode is configured for extravascular implantation within the patient and is coupled to the extravascular ICD by an implantable lead, wherein the shock module is configured to generate an anti-tachyarrhythmia shock and deliver the anti-tachyarrhythmia shock to a patient via the housing electrode and the coil electrode. The signal generator further comprises a TCC transmitter module coupled to housing electrode and the coil electrode, wherein the TCC transmitter module is configured to generate the TCC signal and transmit the TCC signal via the housing electrode and the coil electrode, wherein the TCC signal comprises a biphasic signal having an amplitude and a frequency, wherein at least one of the amplitude or the frequency is configured to avoid stimulation of tissue of the patient by the TCC signal, and wherein the frequency is at least approximately 100 kHz and the amplitude is within a range from approximately 5 mA to approximately 40 mA. The TCC transmitter module comprises a power source configured to deliver a current having the amplitude to the electrodes, polarity switching circuitry coupled to the power source, the polarity switching circuitry configured to switch the polarity of the current at the frequency, and protection circuitry coupled between the power source and the electrodes, wherein the protection circuitry is configured to protect the TCC transmitter module and other circuitry within the housing of the ICD from an anti-tachyarrhythmia shock delivered to the patient by the shock module or an external device. The protection circuitry comprises an LC circuit that comprises a first capacitor coupled between the power source and one of the electrodes and an inductor, wherein the frequency of the TCC signal is within a passband of the LC circuit, and a second capacitor coupled between the power source and the other of the electrodes.

In another example, the disclosure describes an implantable cardioverter defibrillator (ICD) configured to transmit a tissue conduction communication (TCC) signal. The ICD comprises a housing, and means for generating signals within the housing. The means for generating signals comprises means for generating and delivering an anti-tachyarrhythmia shock, and means for generating and transmitting the TCC signal, wherein the TCC signal comprises a biphasic signal having an amplitude and a frequency, wherein at least one of the amplitude or the frequency is configured to avoid stimulation of tissue of the patient by the TCC signal. The means for generating and transmitting the TCC signal comprises means for delivering a current having the amplitude, means for switching the polarity of the current at the frequency, and means for protecting the means for generating and transmitting the TCC signal and other circuitry within the housing of the ICD from an anti-tachyarrhythmia shock delivered to the patient by the means for generating and delivering or an external device.

The details of one or more examples are set forth in the accompanying drawings and the description below. Other features, objects, and advantages will be apparent from the description and drawings, and from the claims.

DETAILED DESCRIPTION

Figure 1:
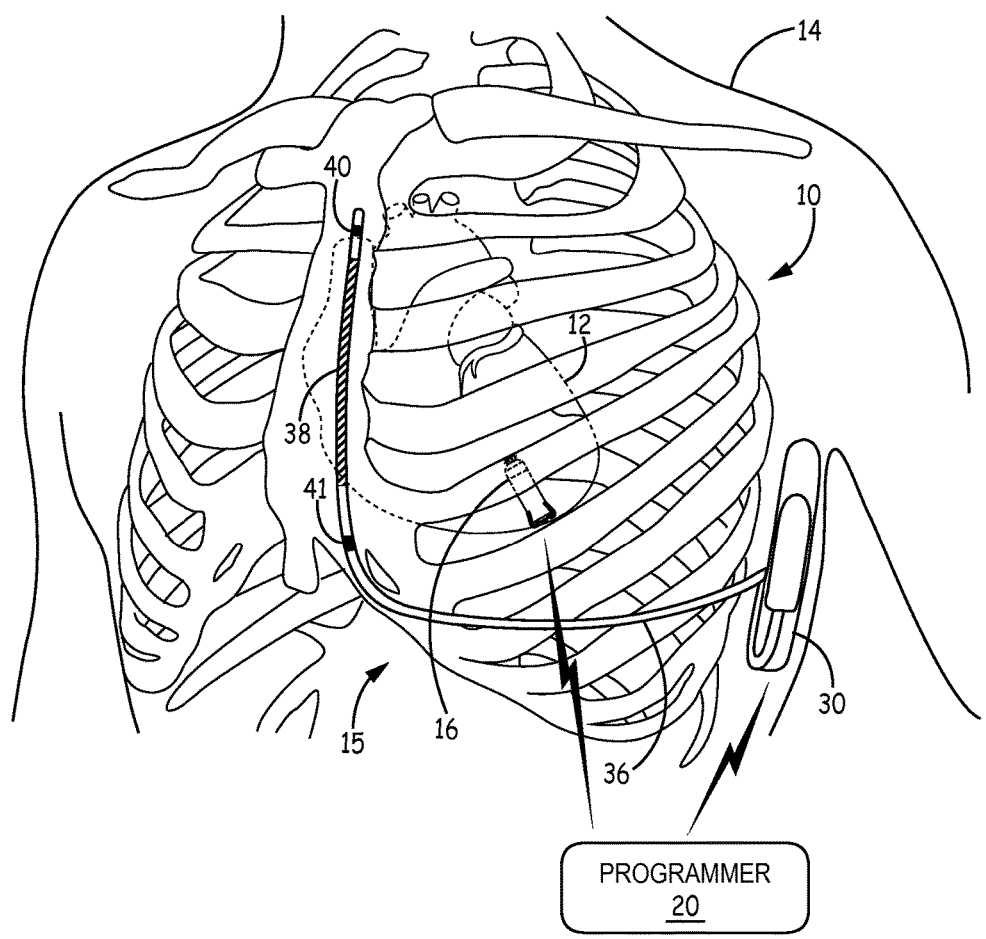
FIG. 1 is a conceptual drawing illustrating an example system that includes an extravascular implantable cardioverter defibrillator (ICD) implanted exterior to the rib cage of a patient and a leadless pacing device (LPD) implanted within a cardiac chamber of the patient.

FIG. 1 is a conceptual drawing illustrating an example cardiac system 10 implanted within a patient 14. Cardiac system 10 includes an extravascular implantable cardioverter defibrillator (ICD) system 15 implanted above the ribcage and sternum, a leadless pacing device (LPD) 16 implanted within a heart 12 of patient 14, and an external programmer 20. ICD 30 of extravascular ICD system 15 and LPD 16 may communicate via tissue conductance communication (TCC). In some examples, the TCC communication may be "one-way" communication, e.g., from ICD 30 to LPD 16, or from LPD 16 to ICD 30. In some examples, the TCC communication may be "two-way" communication. As will be described in further detail herein, ICD 30 may include a signal generator that comprises both a shock module configured to generate a relatively higher-amplitude anti-tachyarrhythmia shock, e.g., a defibrillation or cardioversion shock, for delivery to the patient via electrodes, and a TCC transmitter module configured to generate a relatively lower-amplitude TCC signal for transmission via the patient via the electrodes. The TCC transmitter module may include protection circuitry that allows the delivery of the TCC signal via electrodes, but protects the TCC transmitter module and other circuitry of the ICD from voltages that may develop across the electrodes, such as during delivery of an anti-tachyarrhythmia shock by the ICD or an external defibrillator.

Extravascular ICD system 15 includes ICD 30 connected to at least one implantable cardiac defibrillation lead 36. ICD 30 of FIG. 1 is implanted subcutaneously on the left side of patient 14 under the skin but above the ribcage. Defibrillation lead 36 extends subcutaneously under the skin but above the ribcage from ICD 30 toward a center of the torso of patient 14, bends or turns near the center of the torso, and extends subcutaneously superior under the skin but above the ribcage and/or sternum. Defibrillation lead 36 may be offset laterally to the left or the right of the sternum or located over the sternum. Defibrillation lead 36 may extend substantially parallel to the sternum or be angled lateral from the sternum at either the proximal or distal end.

In other instances, lead 36 may be implanted at other extravascular locations. For example, lead 36 may be implanted at least partially in a substernal location, e.g., between the ribcage and/or sternum and heart. In one such configuration, a proximal portion of lead 36 extends subcutaneously from ICD 30 toward the sternum and a distal portion of lead 36 extends superior under or below the sternum in the anterior mediastinum. The anterior mediastinum is bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 36 extends along the posterior side of the sternum substantially within the loose connective tissue and/or substernal musculature of the anterior mediastinum. Lead 36 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum or ribcage.

Defibrillation lead 36 includes a defibrillation electrode 38 toward the distal portion of defibrillation lead 36, e.g., toward the portion of defibrillation lead 36 extending along the sternum. Defibrillation lead 36 is placed along sternum such that a therapy vector between defibrillation electrode 38 and a housing electrode formed by or on ICD 30 (or other second electrode of the therapy vector) is substantially across a ventricle of heart 12. The therapy vector may, in one example, be viewed as a line that extends from a point on defibrillation electrode 38 (e.g., a center of the defibrillation electrode 38) to a point on the housing electrode of ICD 30. Defibrillation electrode 38 may, in one example, be an elongated coil electrode.

Defibrillation lead 36 may also include one or more sensing electrodes, such as sensing electrodes 40 and 41, located along the distal portion of defibrillation lead 36. In the example illustrated in FIG. 1, sensing electrodes 40 and 41 are separated from one another by defibrillation electrode 38. In other examples, however, sensing electrodes 40 and 41 may be both distal of defibrillation electrode 38 or both proximal of defibrillation electrode 38. In other examples, lead 36 may include more or fewer electrodes. Additionally, the exact configuration, shape, size, and implantation location of ICD 30 may be varied, e.g., from the examples depicted and described herein, for different applications or patients.

As described above, cardiac system 10 also includes at least one LPD 16. In the example illustrated in FIG. 1, LPD 16 provides pacing therapy to heart 18 via a pair of electrodes carried on the housing of pacing device 16. An example LPD is described in U.S. Pat. No. 8,744,572 to Greenhut et al., entitled "SYSTEMS AND METHODS FOR LEADLESS PACING AND SHOCK THERAPY," which issued on Jun. 3, 2014, the entire content of which is incorporated herein by reference. Since LPD 16 includes two or more electrodes carried on the exterior its housing, no other leads or structures need to reside in other chambers of heart 12.

In the example of FIG. 1, LPD 16 is implanted within right ventricle of heart 12 to sense electrical activity of heart 12 and deliver pacing therapy, e.g., ATP therapy, bradycardia pacing therapy, cardiac resynchronization therapy (CRT), and/or post-shock pacing therapy, to heart 12. LPD 16 may be attached to a wall of the right ventricle of heart 12 via one or more fixation elements that penetrate the tissue. These fixation elements may secure LPD 16 to the cardiac tissue and retain an electrode (e.g., a cathode or an anode) in contact with the cardiac tissue. However, in other examples, system 10 may include additional LPDs 16 within respective chambers of heart 12 (e.g., right or left atrium and/or left ventricle). In further examples, LPD 16 may be attached to an external surface of heart 12 (e.g., in contact with the epicardium) such that LPD 16 is disposed outside of heart 12.

This disclosure describes various techniques for facilitating TCC between an ICD, such as ICD 30, and another IMD or external device, such as LPD 16. In some situations, it may be desirable for the two or more IMDs to be able to communicate with each other, e.g., to coordinate, or cooperatively provide, sensing and/or therapy delivery. For example, it may be desirable to allow ICD 30 and LPD 16 to communicate to coordinate delivery of ATP therapy, shocks, and post-shock pacing in response to a tachyarrhythmia detected by one or both of the IMDs.

Extravascular ICD system 15 is configured to detect tachyarrhythmias and deliver anti-tachyarrhythmia shock therapy from one or more electrodes implanted subcutaneously, such as external to the ribcage of the patient. Extravascular ICD system 15 may thus deliver shocks to the patient without any leads implanted within the vasculature and/or heart of the patient. However, the absence of endocardial or epicardial electrodes may decrease the ability of extravascular ICD system 15 to provide, or the desirability of the extravascular ICD system providing, pacing therapy to the patient, such as ATP and post-shock pacing.

As discussed above, one or more LPDs 16 carrying one or more electrodes may be implanted within various chambers of the heart of the patient or otherwise in close proximity of the cardiac muscle. At such locations, LPD 16 may sense cardiac electrogram signals with high signal-to-noise ratios to detect arrhythmias. In addition, LPD 16 may provide cardiac pacing at the location of the implanted LPD. However, LPD 16 may not be capable of delivering an anti-tachyarrhythmia shock or sensing far-field cardiac electrogram signals indicative of global cardiac condition.

Extravascular ICD system 15 and one or more LPDs 16 may be co-implanted, as illustrated in the case of cardiac system 10 of FIG. 1, and ICD 30 and LPD 16 may communicate to enable a system level of functionality such as sharing the detection of arrhythmias between devices, synchronized timing of anti-tachyarrhythmia shocks, ATP, and/or post-shock pacing, and optimization of the resources (e.g., battery capacity or processing power) available to each device. In some examples, communication between the ICD 30 and LPD 16 may be used to initiate therapy and/or confirm that therapy should be delivered. One approach is for ICD 30 to function as the "master" and LPD 16 to function as the "slave" in a "master-slave" relationship. In such examples, LPD 16 would need to receive a signal from ICD 30 prior to delivering cardiac pacing therapy.

For example, ICD 30 may detect a tachyarrhythmia and determine to deliver a shock to patient 14 to treat the tachyarrhythmia. In some examples, ICD 30 may be configured to, in response to the determination to deliver the shock, transmit a command or other communication requesting LPD 16 to deliver ATP. Delivery of ATP may be performed in an attempt to terminate the tachyarrhythmia prior to needing to deliver a shock. Since ICD 30 may require a period of time to charge prior to the ICD being capable of delivering the shock, the ATP may not delay the delivery of the shock.

In one example, ICD 30 may be configured to continually monitor electrical signals of heart 12 for tachyarrhythmias. ICD 30 may detect, based on a sensed electrical signal, a tachyarrhythmia eligible for anti-tachyarrhythmia shock therapy and/or ATP. In response to this detection, ICD 30 may a transmit communication to LPD 16 to deliver ATP. In such examples, ICD 30 may cause LPD 16 to "wake up" from an at least partially inactive state to an active state. LPD 16 may be set to inactive if it is not needed to treat conditions such as bradyarrhythmias in patient 14. However, if LPD 16 is required to monitor and/or treat bradyarrhythmias, LPD 16 may remain active to detect and/or treat tachyarrhythmias as well.

In addition to the delivery of ATP, LPD 16 may be configured to deliver post-shock pacing to heart 12. After delivery of an anti-tachyarrhythmia shock, heart 12 may benefit from pacing to return to a normal sinus rhythm, e.g., if heart 12 has developed bradycardia or asystole, or otherwise recover from receiving the shock. In some examples, LPD 16 and/or ICD 30 may be configured to detect bradycardia or asystole, e.g., after delivery of a shock to terminate a tachyarrhythmia. In some examples, this post-shock pacing therapy may be automatically delivered by LPD 16 in response to detecting a shock, or the resulting bradycardia or asystole. In some examples, after ICD 30 delivers one or more shocks, ICD 30 may transmit a command to LPD 16 instructing LPD 16 to deliver post-shock pacing, e.g., in response to determining that a delivered shock terminated a tachyarrhythmia or detecting bradycardia or asystole resulting from a delivered shock.

In some examples, LPD 16 may transmit a communication message to ICD 30. For example, LPD 16 may first detect, or in response to a query from ICD 30 confirm, a tachyarrhythmia eligible for an anti-tachyarrhythmia shock and/or ATP therapy. In some examples, LPD 16 may command the ICD 30 to deliver one or more shocks in response to a tachyarrhythmia detected by LPD 16.

Because there are no wires connecting ICD 30 to LPD 16, ICD 30 and LPD 16 may use a wireless communication technique to remain synchronized and prevent device-to-device interference. Wireless techniques for IMD communication include RF telemetry, inductive telemetry, acoustics, and TCC. During TCC, current is driven through the tissue between two or more electrodes of the transmitting IMD (or external device), e.g., between two or more of defibrillation electrode 38, an electrode formed on or by the housing of ICD 30, sensing electrode 40, or sensing electrode 41 of extravascular ICD system 15. The current spreads through the thorax, producing a potential field. The receiving IMD (or external device) may detect the TCC signal by measuring the potential difference between two of its electrodes, e.g., the pacing tip and sense ring of LPD 16.

TCC may be a desired technique for inter-IMD communication. The current used to generate the TCC signal must be of sufficient amplitude to be detected by another device, but should at the same time not capture tissue, e.g., nerve or muscle tissue, or cause pain. Additionally, the TCC signal is generated by driving current through the tissue between two electrodes connected to the patient. The circuitry used to generate the TCC signal is not, in general, capable of withstanding the high voltages that can generated between the electrodes implanted within the patient. Therefore, additional circuitry must be added to protect the TCC signal generation circuitry and other circuitry inside of the ICD from exposure to relatively high voltages across the electrodes, such as during delivery of a defibrillation shock by the ICD or an external defibrillator, an electrocautery procedure, or magnetic resonance imaging. Also, it is generally desirable for an IMD to be as small as possible. Therefore, the size of the circuitry and components within a housing of the IMD should be constrained to the extent possible. Additionally, the power required by such circuitry and components should be constrained to the extent possible.

Generally, this disclosure describes various techniques for facilitating transmission of TCC signals by an ICD, such as ICD 30 in an extravascular ICD system 15. More particularly, the this disclosure describes ICDs that include a signal generator that comprises both a shock module configured to generate a relatively higher-amplitude defibrillation or cardioversion shock for delivery to the patient, and a TCC transmitter module configured to generate a relatively lower-amplitude TCC signal for transmission via the patient. The TCC signal may comprise a biphasic signal having an amplitude and a frequency, wherein the amplitude and/or the frequency are configured to avoid stimulation of tissue of the patient.

Both the anti-tachyarrhythmia shock and the TCC signal may be delivered via the same electrodes, such as coil electrode 38 and a housing electrode of ICD 30. In normal operation of the ICD, a relatively high voltage is applied to the coil electrode 38 and housing electrode of ICD 30 when a defibrillation shock is delivered. In addition, due to the size of, and spacing between implanted electrodes used by ICD 30 to deliver relatively higher voltage defibrillation or cardioversion shocks, there may be a relatively higher voltage that develops across these electrodes in other situations, such as during external defibrillation by an external defibrillator, an electrocautery procedure, or magnetic resonance imaging. The TCC transmitter module may include protection circuitry to protect the TCC transmitter module and other ICD circuitry from such voltages. The protection circuitry may be configured to pass the TCC signal, while still protecting the ICD circuitry from voltages on the electrodes.

In some examples, the TCC signal is capacitively coupled to the electrodes. In such examples, the protection circuitry includes capacitors respectively coupled to each of the electrodes. The capacitors may protect against the relatively transient high-voltages associated with anti-tachyarrhythmia shocks. In some examples, the one or more of the capacitors are coupled to one or more inductors, and the protection circuitry comprises one or more LC circuits. The one or more LC circuits may be tuned to provide a pass-band that includes the frequency of the TCC signal. In some examples, the TCC signal is delivered to the electrodes by high-voltage switches, and the protection circuitry comprises such switches. In general, TCC transmitter modules according to this disclosure may be both able generate a relatively low amplitude TCC signal at a desired frequency for transmission via defibrillation electrodes, and include protection circuitry to protect such circuitry from relatively high amplitude anti-tachyarrhythmia shocks.

Additionally, in some examples, the TCC transmitter module may include circuitry used by other modules of the signal generator, such as circuitry used by a shock module to generate and deliver anti-tachyarrhythmia shocks via the electrodes and/or circuitry used by a fibrillation induction module to deliver a signal via the electrodes that induces fibrillation. The use of such circuitry by the TCC transmitter module may advantageously facilitate a relatively smaller number or volume of circuit components, and accordingly size and power consumption, of ICD 30.

Although primarily described with respect to examples in which an ICD and LPD communicate to facilitate delivery of ATP and/or post-shock pacing, the techniques described in this disclosure may be implemented in other examples for other reasons and/or to facilitate communication between other coexistent systems. For example, although described primarily in the context of an extravascular ICD, the techniques of this disclosure may be implemented in an ICD coupled to one or more transvascular and/or endocardial leads. In some examples, the techniques of this disclosure may be implemented to facilitate TCC between an ICD, such as an ICD coupled to one or more transvascular and/or endocardial leads, and one or more LPDs, e.g., to facilitate delivery of CRT by the one or more LPDs alone, or in combination with the ICD. As another example, the techniques of this disclosure may be implemented to facilitate TCC between an ICD and an implantable neurostimulator, e.g., to control the timing of the neurostimulation, or an implantable physiological monitor, e.g., to control the timing of physiological monitoring or to receive measured values from the monitor. In some examples, the techniques of this disclosure may be implemented to facilitate TCC between ICD 30 and an external device, e.g., for programming the ICD and/or retrieving information from the ICD, or testing the ability of ICD 30 to communication via TCC, such as during implantation of the ICD. As such, the example of FIG. 1 is illustrated for exemplary purposes only and should not be considered limiting of the techniques described herein.

Figure 2:
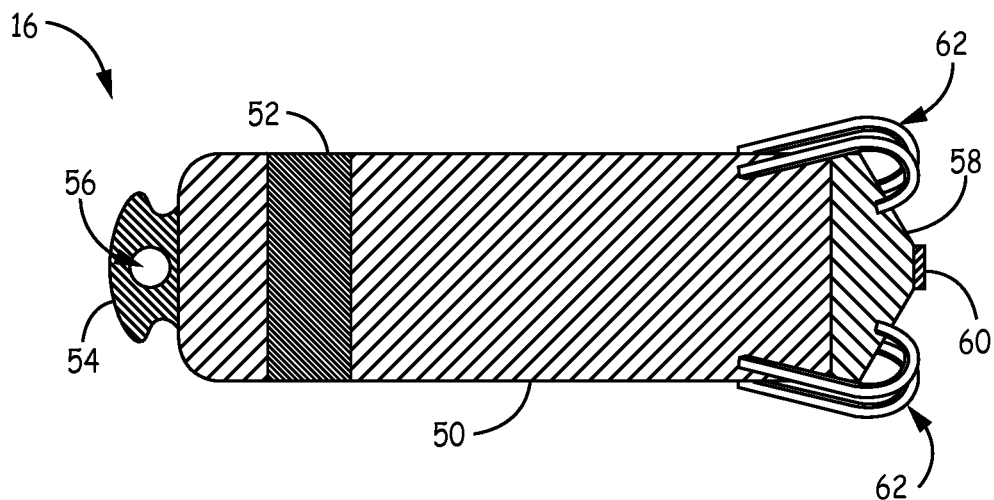
FIG. 2 is a conceptual drawing illustrating the example LPD of FIG. 1.

FIG. 2 is a conceptual drawing further illustrating LPD 16. As shown in FIG. 2, LPD 16 includes case 50, cap 58, electrode 60, electrode 52, fixation mechanisms 62, and flange 54 defining opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including two electrodes 52 and 60, LPD 16 may typically include two or more electrodes to deliver an electrical signal (e.g., therapeutic signals such as pacing pulses and/or a TCC signal) and/or provide at least one sensing vector for sensing a cardiac electrogram and/or a TCC signal.

Electrodes 52 and 60 are carried on the housing created by case 50 and cap 58. In this manner, electrodes 52 and 60 may be considered leadless electrodes. In the example of FIG. 2, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating.

Electrode 60 may be used as a cathode and electrode 52 may be used as an anode, or vis-a-versa, for cardiac pacing therapy, such as ATP or post-shock pacing, or transmitting TCC signals. In addition, electrodes 52 and 60 may be used to detect intrinsic electrical signals from cardiac muscle. In other examples, LPD 16 may include three or more electrodes, where any two or more of the electrodes may form a vector for delivery of therapy, detecting intrinsic signals, transmitting TCC signals, and receiving TCC signals. In some examples in which LPD 16 includes three or more electrodes, the LPD may select two or more of the electrodes, e.g., via switches, to form a vector for TCC. LPD 16 may use multiple vectors for TCC to, for example, provide signal or vector diversity, which may improve the quality or reliability of TCC.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 2, fixation mechanisms 62 may be constructed of a shape memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

Figure 3:
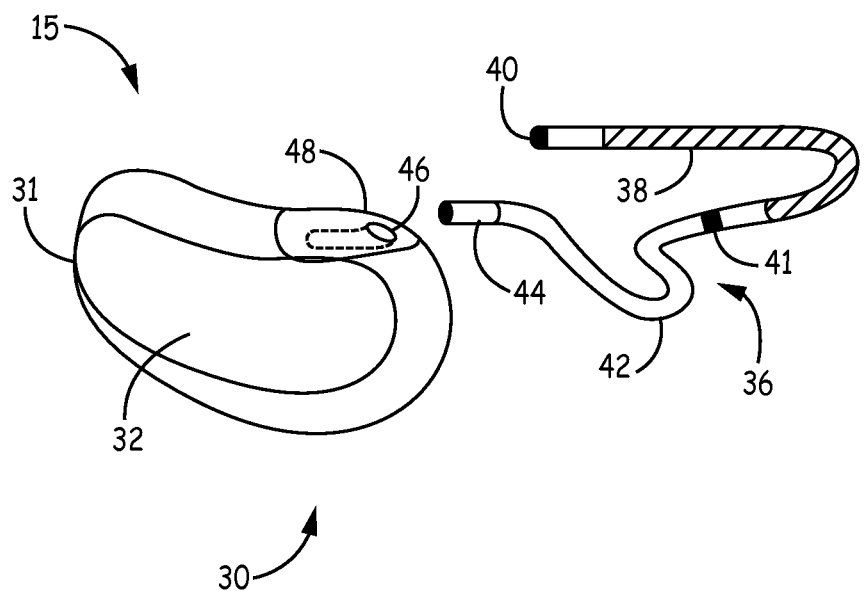
FIG. 3 is a conceptual drawing illustrating the example extravascular ICD of FIG. 1

FIG. 3 is a conceptual drawing further illustrating ICD 30 of FIG. 1. In the example of FIG. 3, housing 31 may be constructed as an ovoid with a substantially kidney-shaped profile. The ovoid shape of housing 31 may promote ease of subcutaneous implantation and may minimize patient discomfort during normal body movement and flexing of the thoracic musculature. In other examples, housing 31 may be constructed with different shapes intended for different implant locations and/or to house different components, or to be coupled to different subcutaneous leads.

Housing 31 may contain the electronic circuitry of ICD 30. Defibrillation lead 36 may include distal defibrillation coil electrode 38, distal sensing electrode 40, proximal sensing electrode 41, insulated flexible lead body 42 and proximal connector pin 44. Proximal connector pin 44 of lead 36 may be inserted into connector 46 of header 48. Header 48 and connector 46 of ICD 30, and connector pin 44 at a proximal end of defibrillation lead 36, may provide electrical connections between electrodes 38, 40, and 41 of lead 36, and the circuitry within housing 31 of ICD 30. Defibrillation lead 36 includes one or more conductors that form an electrically conductive path within the lead body and interconnect the electrical connections and respective ones of the electrodes. In some examples, housing 31, or a portion thereof, may be configured as an electrically conductive surface and operate as an electrode 32, e.g., a can or housing electrode 32, for delivery of electrical signals and/or sensing.

ICD 30 may sense intrinsic electrical signals, e.g., a cardiac electrogram, from one or more sensing vectors formed by two or more of electrodes 32, 38, 40 and 41, such as one or more sensing vectors that include combinations of electrodes 40 and 41 and housing electrode 32. For example, ICD 30 may obtain electrical signals sensed using a sensing vector between electrodes 40 and 41, obtain electrical signals sensed using a sensing vector between electrode 40 and housing electrode 32 of ICD 30, obtain electrical signals sensed using a sensing vector between electrode 41 and housing electrode 32 of ICD 30, or a combination thereof. In some instances, ICD 30 may even sense cardiac electrical signals using a sensing vector that includes defibrillation electrode 38 and one of electrodes 40 and 41 or housing electrode 32 of ICD 30.

The sensed electrical intrinsic signals may include electrical signals generated by cardiac muscle and indicative of depolarizations and repolarizations of heart 12 at various times during the cardiac cycle. Additionally, the sensed electrical signals may also include electrical signals, e.g., pacing pulses, generated and delivered to heart 12 by LPD 16. ICD 30 analyzes the electrical signals sensed by the one or more sensing vectors to detect tachyarrhythmia, such as ventricular tachycardia or ventricular fibrillation. In response to detecting the tachyarrhythmia, ICD 30 may begin to charge a storage element, such as a bank of one or more capacitors, and, when charged, deliver one or more anti-tachyarrhythmia shocks via defibrillation electrode 38 of defibrillation lead 36 if the tachyarrhythmia is still present and determined to require anti-tachyarrhythmia shock therapy.

ICD 30 also delivers anti-tachyarrhythmia shocks via a vector formed by two or more of the electrodes, such as defibrillation electrode 38 and housing electrode 32. ICD 30 may also transmit TCC signals via a vector formed by two or more of the electrodes, such as electrode 38 and housing electrode 32. In some examples, ICD 30 may select two or more of the electrodes, e.g., via switches, to form a vector for TCC. ICD 30 may use multiple vectors for TCC to, for example, provide signal or vector diversity, which may improve the quality or reliability of TCC.

Figure 4:
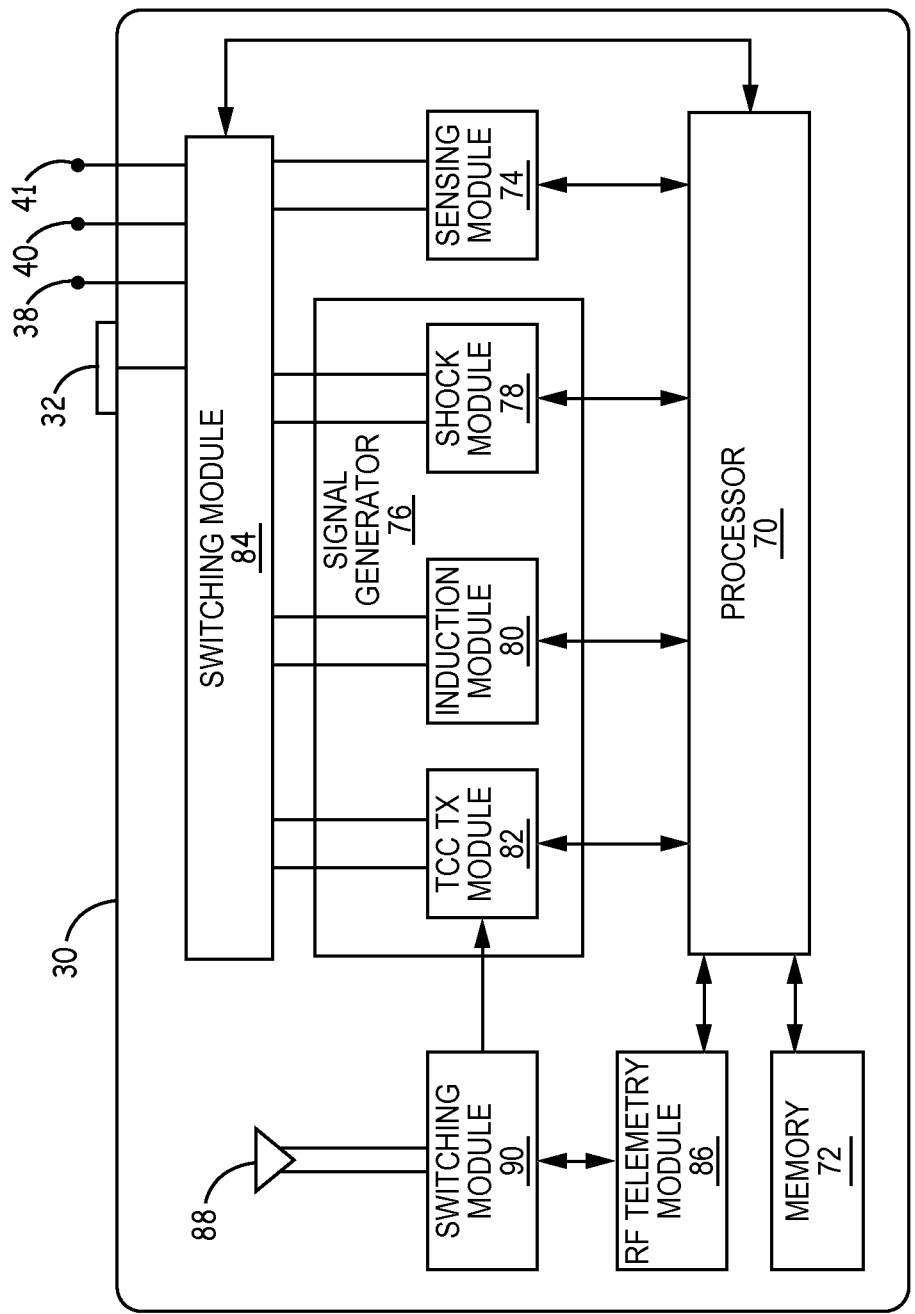
FIG. 4 is a functional block diagram illustrating an example configuration of the extravascular ICD of FIG. 1.

FIG. 4 is a functional block diagram illustrating an example configuration of ICD 30 of FIG. 1. In the illustrated example, ICD 30 includes a processor 70, memory 72, sensing module 74, and signal generator 76. Memory 72 includes computer-readable instructions that, when executed by processor 70, cause ICD 30 and/or processor 70 to perform various functions attributed to ICD 30 and processor 70 herein (e.g., detection of tachyarrhythmias, communication with LPD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Electrical sensing module 74 is configured to monitor signals from two or more of electrodes 32, 38, 40 and 41 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 74 may use a switching module 84 to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via switching module 84. Sensing module 74 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Processor 70 may implement interval counters, which may be reset upon sensing of R-waves and P-waves by sensing module 74. The value of the count present in the interval counters when reset by sensed R-waves and P-waves may be used by processor 70 to measure the durations of R-R intervals, P-P intervals, P-R intervals and R-P intervals, which are measurements that may be stored in memory 72. Processor 70 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 72 may be configured as a plurality of recirculating buffers, capable of holding series of measured intervals, which may be analyzed by processor 70 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processor 70 in other examples.

As illustrated in FIG. 4, signal generator 76 includes a shock module 78. Shock module 78 is configured to deliver anti-tachyarrhythmia shocks, e.g., defibrillation and/or cardioversion shocks, to patient 14. The anti-tachyarrhythmia shocks are configured to correct a tachyarrhythmia of heart 12, such as fibrillation and/or tachycardia. In response to detecting a tachyarrhythmia treatable with an anti-tachyarrhythmia shock, such as a fibrillation treatable with a defibrillation shock, processor 70 controls shock module 78 to deliver the anti-tachyarrhythmia shock.

Shock module 78 includes circuitry configured to deliver therapeutic shocks. For example, shock module 78 may include an energy storage element, such as one or more capacitors, configured to store the energy for the therapeutic shock. In some examples, in response to detecting a treatable tachyarrhythmia, processor 70 controls shock module 78 to charge the energy storage element to prepare for delivering an anti-tachyarrhythmia shock and then, e.g., in response to confirming the tachyarrhythmia, may control the shock module to discharge the energy storage element to deliver the shock to patient 14. Shock module 78 may include other circuitry, such as circuitry to charge the energy storage element, and switches to change the polarity of the shock to provide a bi-phasic or multi-phasic shock. Shock module 78 may include a variety of voltage level-shifting circuitry, switches, transistors, diodes, or other circuitry. The switches may comprise transistors.

Shock module 78 delivers the anti-tachyarrhythmia shock to patient 14 via two or more electrodes, such as defibrillation electrode 38 and housing electrode 32. In the illustrated example, shock module 78 may be coupled to any of electrodes 32, 38, 40, and 41 through switching module 84. However, shock module 78 generally will deliver anti-tachyarrhythmia shocks via defibrillation electrode 38 and housing electrode 32, which may have a larger surface area than sensing electrodes 40 and 41. In some examples, shock module 78 will not be connectable to sensing electrodes 40 and 41 via switching module 84. In some examples, switching module 84 includes switches that change the connection of the energy storage element of shock module 78 during a shock to change the polarity of the shock.

In the example illustrated by FIG. 4, signal generator 76 also includes an induction module 80. Induction module 80 is configured to deliver an induction signal to patient 14 to induce a fibrillation of heart 12. The induction signal may be an alternating signal, and induction module 80 may generate the induction signal with an amplitude, frequency, and/or timing relative to the cardiac cycle, such that the induction signal induces fibrillation of heart 12. In some examples, the induction signal may be a 50 Hz signal timed to occur proximate to or during repolarization of heart 12.

Processor 70 controls induction module 80 to generate the induction signal, e.g., in response to a command from programmer 20 (FIG. 1). Fibrillation induction may be desired to test the ability of ICD 30 to terminate fibrillation, and the threshold shock energy level required to terminate fibrillation. Fibrillation induction may occur during a procedure to implant ICD system 15.

Induction module 80 includes circuitry configured to deliver the induction signal. For example, induction module 80 may include switches and/or transistors configured to be switched fast enough to produce an alternating signal with a frequency that will induce fibrillation of heart 12. Induction module 80 may also include circuitry to provide the current for the induction signal, or to otherwise condition the induction signal prior to delivery to patient 14. Induction module 80 delivers the induction signal to patient 14 via two or more electrodes, such as defibrillation electrode 38 and housing electrode 32. In the illustrated example, induction module 80 may be coupled to any of electrodes 32, 38, 40, and 41 through switching module 84. However, induction module 80 generally will deliver induction signals via defibrillation electrode 38 and housing electrode 32. In some examples, induction module 80 will not be connectable to sensing electrodes 40 and 41 via switching module 84.

In the example of FIG. 4, signal generator 76 also includes TCC transmitter (TX) module 82. TCC transmitter module 82 is configured to generate and transmit a TCC signal, e.g., to communicate with LPD 16, another IMD, or an external device, such as programmer 20. The TCC signal is an alternating signal having an amplitude and/or frequency configured to avoid stimulation of tissue of patient 14. In some examples, switching module 84 may be configured to selectively couple TCC transmitter module 82 to any two or more of electrodes 32, 38, 40 and 41, e.g., housing electrode 32 and defibrillation electrode 38, for transmission of a TCC signal.

In some examples, the frequency of the TCC signal is greater than approximately 100 kilohertz (kHz). A biphasic current waveform, such as a TCC signal emitted or received by electrodes 52 and 60, at a frequency of at least approximately 100 kHz may be less likely to stimulate nearby tissue, e.g., muscles or nerves, or cause pain than lower frequency waveforms. Consequently, a TCC signal having a frequency of at least approximately 100 kHz may have a higher amplitude than a lower frequency signal, which may increase the likelihood that LPD 16, or another implanted or external device, may receive the TCC signal from ICD 30. The amplitude of the TCC signal may be within a range from approximately 5 milliamps (mA) to approximately 40 mA, such as within a range from approximately 5 mA to approximately 10 mA. In some examples, the amplitude of the TCC signal may be approximately 10 mA. A TCC signal having a frequency of at least approximately 100 kHz and an amplitude no greater than approximately 10 mA may be unlikely to stimulate nearby tissue, e.g., muscles or nerves, or cause pain.

In some examples, LPD 16 is configured to selectively couple its RF telemetry receiver to either an antenna to receive RF telemetry signals, or electrodes to receive TCC signals. Using the RF telemetry receiver of the LPD for these two purposes may reduce the number and size of components within the LPD, and thereby allow a reduction in the overall volume of LPD 16. In such examples, the TCC signal may be within a predetermined frequency band for RF telemetry communication, which may be at least approximately 100 kHz. In some examples, the predetermined frequency band for RF telemetry communication may be within a range from approximately 150 kHz to approximately 200 kHz.

The modulation of the TCC signal may be, as examples, amplitude modulation (AM), frequency modulation (FM), or digital modulation (DM), such as frequency-shift keying (FSK) or phase-shift keying (PSK). In some examples, the modulation is FM toggling between approximately 150 kHz and approximately 200 kHz. In some examples, the TCC signal has a frequency of 150/200 kHz and is modulated using FSK modulation at 12.5 kbps. The data modulated on TCC signals, e.g., to LPD 16, may include "wake up" commands, or commands to deliver ATP or post-shock pacing, as examples.

The configuration of ICD 30 including TCC transmitter module 82 illustrated in FIG. 4 makes ICD 30 capable of "one-way" or uni-directional TCC as a transmitter. Such a configuration may be used if, for example, ICD 30 is configured as a master to another IMD, e.g., LPD 16 to provide commands for ATP and post-shock pacing as described herein, in a master-slave relationship. In some examples, ICD 30 may additionally or alternatively include a separate TCC receiver module to facilitate "two-way" TCC between ICD 30 and LPD 16. The separate TCC receiver module may have more sensitivity than an RF telemetry receiver module, e.g., to compensate for lower signal-to-noise ratio signals from LPD 16. LPD 16 may generate relatively lower signal-to-noise ratio signals by generating relatively smaller amplitude signals. LPD 16 may generate relatively smaller amplitude signals due to its smaller power source, and/or to avoid stimulation of adjacent tissue because electrodes 50 and 62 of LPD 16 may have a relatively short separation distance and/or small surface area and, accordingly, higher current density for a given signal amplitude.

Additionally, although described primarily with respect to examples in which TCC from ICD 30 to LPD 16 is to command LPD 16 to deliver cardiac pacing, the TCC may additionally or alternatively be for other purposes. For example, ICD 30 and/or LPD 16 may transmit and/or receive TCC signals to test the operation of TCC. In one example, ICD 30 may send a TCC message to LPD 16 to shorten a pacing interval for one or more beats, and detect implementation of the shortened pacing interval by detecting pacing pulses or resulting depolarizations with sensing module 74 via one or more of electrodes 32, 38, 40, or 41. Based on detecting the shortened pacing interval, ICD 30 may confirm the availability of TCC with LPD 16.

In some examples, signal generator 76, including shock module 78 and induction module 80, may be considered to be, or considered to include, a high-voltage (HV) module or circuitry. Signal generator 76 may be considered an HV module in the sense that shock module 78 and induction module 80, and their respective circuitry, are configured to generate and deliver relatively higher voltage signals, e.g., in comparison to the TCC signal or pacing pulses. Consequently, the inclusion of TCC transmitter module 82 in signal generator 76 may be considered a modification of the HV module or circuitry to include the ability to generate and transmit relatively lower voltage TCC signals. In some examples, TCC transmitter module 82 may include or use circuitry that is also used to provide shock module 78 and/or induction module 80.

Memory 72 may be configured to store a variety of operational parameters, therapy parameters, sensed and detected data, and any other information related to the monitoring, therapy and treatment of patient 14. Memory 72 may store, for example, thresholds and parameters indicative of tachyarrhythmias and/or therapy parameter values that at least partially define delivered anti-tachyarrhythmia shocks. In some examples, memory 72 may also store communications transmitted to and/or received from LPD 16, or another device.

As illustrated in FIG. 4, ICD 30 also includes an RF telemetry module 86 and antenna 88. Antenna 88 comprises any one or more antenna elements configured to wirelessly receive and emit RF signals. In some examples, antenna 88 may comprise a plurality of antennas or antenna elements, selectable via switches, to provide antenna or signal diversity, which may improve the quality or reliability of RF telemetry communication.

RF telemetry module 86 may include circuitry configured to receive, via antenna 88, and demodulate alternating signals within the predetermined frequency band for RF telemetry communication. The data modulated on RF telemetry signals may be instructions from programmer 20, for example. RF telemetry module 86 also includes circuitry configured to modulate and transmit, via antenna 88, an RF telemetry signal. The RF telemetry signals may be within the predetermined frequency band for RF telemetry communication.

RF telemetry module 86 may include an oscillator and/or other circuitry configured to generate a carrier signal at the desired frequency. RF telemetry module 86 further includes circuitry configured to modulate data, e.g., stored physiological and/or therapy delivery data, on the carrier signal. The modulation of RF telemetry signals may be, as examples, AM, FM, or DM, such as FSK or PSK.

In some examples, RF telemetry module 86 is configured to modulate the TCC signal for transmission by TCC transmitter module 82. In the example illustrated by FIG. 4, ICD 30 includes a switching module 90 configured to selectively couple RF telemetry module 86 to antenna 88 or TC transmitter module 82. In some examples, although RF telemetry module 86 modulates both RF telemetry and TCC signals within the same frequency band, e.g., within a range from approximately 150 kHz to approximately 200 kHz, the modulation techniques for the two signals may be different. For example, RF telemetry module 86 may modulate RF telemetry signals at 175 kHz using PSK modulation at 87.5 kilo-bytes per second (kbps), and modulate TCC signals at 150 kHz/200 kHz using FSK modulation at 12.5 kbps. In some examples, an element of TCC transmitter module 82, or another element of signal generator 76, modulates the TCC signal, rather than RF telemetry module 86.

Figure 5:
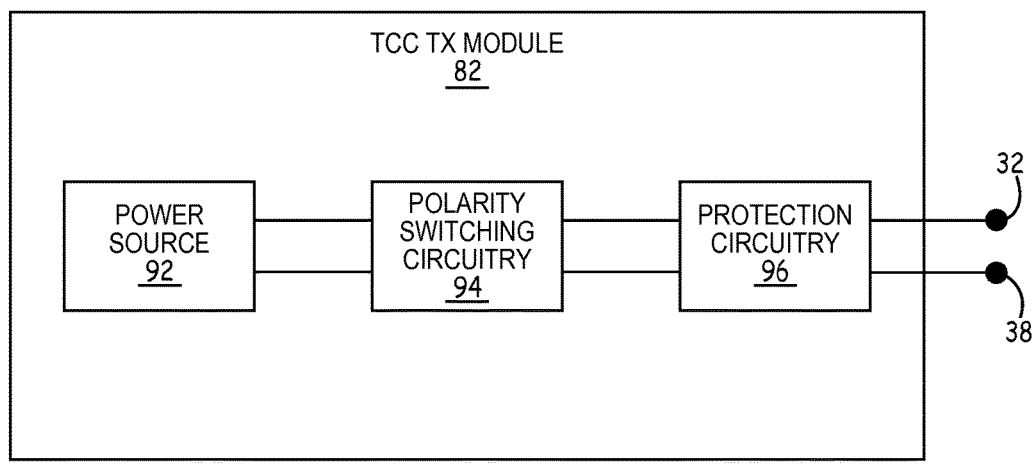
FIG. 5 is a functional block diagram illustrating an example configuration of the tissue conduction communication (TCC) transmitter module of the extravascular ICD of FIG. 1.

FIG. 5 is a functional block diagram illustrating an example configuration of TCC transmitter module 82 of ICD 30. In the example illustrated by FIG. 5, TCC transmitter module 82 includes a power source 92, polarity switching circuitry 94, and protection circuitry 96. In the illustrated example, TCC transmitter module 82 is coupled to defibrillation electrode 38 and housing electrode 32. In other examples, TCC transmitter module 82 may be coupled to other electrodes, e.g., via switching module 84 (FIG. 4).

Power source 92 may include a voltage source and/or a current source configured to produce and/or deliver a TCC signal current through the electrodes having a desired amplitude, e.g., high enough to be detected by LPD 16 or another device, but low enough to avoid stimulation of tissue, e.g., within a range from approximately 5 mA to approximately 40 mA, such as approximately 10 mA, as discussed above. In some examples, assuming the load presented by the tissue of patient 14 between the electrodes is approximately 50 ohm, power source 92 may capable of producing a current having the desired amplitude for the TCC signal through the approximately 50 ohm resistive load connected between the electrodes.

Polarity switching circuitry 94 is coupled to power source 92, and includes circuitry configured to switch the polarity of the TCC signal current at a frequency of the TCC signal. For example, polarity switching circuitry 94 may include transistors and/or switches configured to switch the polarity of the current at the frequency. In some examples, polarity switching circuitry comprises a respective one or more transistors and/or switches coupled to each of electrodes 32, 38, and the on-off states of the respective transistor(s) and/or switch(es) are alternated to switch the polarity of the TCC signal current between the electrodes at the frequency.

As discussed above, the frequency may be at least approximately 100 kHz. For example, the frequency may be within a range from approximately 150 kHz to approximately 200 kHz. In some examples, polarity switching circuitry 94 may be configured to toggle the frequency between approximately 150 kHz and approximately 200 kHz.

Protection circuitry 96 is coupled between power source 92 and electrodes 32, 38. Protection circuitry 96 may be configured to protect the circuitry inside housing 31 of ICD 30, such as relatively lower-voltage circuitry, including TCC transmitter module 82, against relatively high voltages developed across the electrodes, e.g., such as voltages produced by an anti-tachyarrhythmia shock delivered by shock module 78 or an external device, such as an external defibrillator. The circuitry within housing 31 of ICD 30 protected by protection circuitry 96 may include circuitry of any of the components of ICD 30 illustrated in FIG. 4, such as circuitry of processor 70, memory 72, sensing module 74, signal generator 76, shock module 78, induction module 80, TCC transmitter module 82, switching module 84, RF telemetry module 86, and switching module 88. ICDs have included circuits designed to allow high voltage therapy to be delivered between two electrodes while protecting the ICD circuitry from high voltages from external sources. ICD 30 configured according to the techniques this disclosure may be further configured to deliver a lower voltage signal, as compared to anti-tachyarrhythmia shocks, between the same electrodes, while still protecting the circuitry from large voltages, such as presented by anti-tachyarrhythmia shocks.

TCC transmitter module 82, e.g., protection circuitry 96, may be configured to permit the transmission of a low-voltage signal through the tissue while still protecting circuitry of ICD 30 from high voltages, such as high-voltage anti-tachyarrhythmia shocks. In some examples, protection circuitry 96 is configured to protect against voltages, i.e., provide a standoff voltage, of at least approximately 2000 volts. In some examples, protection circuitry 96 is configured to provide a stand-off voltage of at least approximately 3200 volts.

Protection circuitry 96 may include, as examples, capacitors, inductors, switches, resistors, and/or diodes. In some examples, protection circuitry 96 includes a first capacitor coupled between power source 92 and one of electrodes 32, 38, and a second capacitor coupled between power source 92 and the other of electrodes 32, 38. In such examples, the TCC signal may be capacitively coupled to electrodes 32, 38.

In such examples, protection circuitry 96 may additionally include at least one inductor coupled to one of the capacitors to provide an LC circuit. In some examples, each of the capacitors is coupled to one or more inductors to provide respective LC circuits coupled to electrodes 32, 38. The frequency of the TCC signal may be within a pass-band of the one or more LC circuits, which may be greater than approximately 100 kHz, such as within a range from approximately 150 kHz to approximately 200 kHz.

In some examples, protection circuitry 96 includes respective high-voltage switches coupled to electrodes 32, 38. The switches may source current at the amplitude for the TCC signal. In some examples, the on-off states of the switches may be toggled to alternate the current at the frequency of the TCC signal. In this manner, switches may form part of one or more of power source 92, e.g., as a current source, polarity switching circuitry 94, and protection circuitry 96.

In some examples, TCC transmitter module 82 is configured to increase the maximum current of the TCC signal by shaping the waveform of the TCC signal. By having the transmitted current waveform ramp up to its maximum over a plurality of cycles, it is predicted that higher peak currents can be achieved without reaching the threshold for tissue stimulation and/or pain. In such examples, power source 92 may be configured to ramp up the amplitude of voltage or current over a plurality of cycles.

Additionally, TCC transmitter module 82 may be configured to transmit a message via a TCC signal a plurality of times throughout a cardiac cycle. Multiple transmissions at different times during the cardiac cycle increase the likelihood that the message is sent during both systole and diastole to make use of cardiac motion to reduce the chance that LPD 16 is in a poor orientation for receiving signals. Multiple transmissions at different times during the cardiac cycle may thereby increase the likelihood that that the message is received.

In some examples, as discussed above, RF telemetry module 86 may be configured to modulate the TCC signal. In some examples, the modulation of the signal by RF telemetry module 86 controls one or both of power source 92 and polarity switching circuitry 94 to generate the TCC signal with an amplitude and/or frequency according to the encoding. For example, the encoding by RF telemetry module 86 may control polarity switching circuitry 94 to change the polarity of the current signal at frequencies within a range from approximately 150 kHz to approximately 200 kHz according to FM. As another example, the encoding by RF telemetry module 86 may control polarity switching circuitry 94 to change the polarity of the current signal at either approximately 150 kHz or approximately 200 kHz to toggle the frequency according to FSK modulation. In some examples, RF telemetry module 86 may include a mixed signal integrated circuit, or other circuitry, configured to provide a digital version of the modulated TCC signal to a controller, or other circuitry, TCC transmitter module 82, which may control one or both of current source 92 and polarity switching circuitry 94 to generate the TCC signal with an amplitude and/or frequency according to the modulation. In other examples, TCC transmitter module 82 may include a controller, or other circuitry, configured to modulate the TCC signal.

In this manner, ICD 30, including TCC transmitter module 82 is an example of an ICD configured to transmit a TCC signal, the ICD comprising a housing, and a signal generator within the housing. The signal generator comprises a shock module coupled to a plurality of electrodes, wherein the shock module is configured to generate an anti-tachyarrhythmia shock and deliver the anti-tachyarrhythmia shock to a patient via the plurality of electrodes, and a TCC transmitter module coupled to the plurality of electrodes, wherein the TCC transmitter module is configured to generate the TCC signal and transmit the TCC signal via the plurality of electrodes, wherein the TCC signal comprises a biphasic signal having an amplitude and a frequency, wherein at least one of the amplitude and the frequency are configured to avoid stimulation of tissue of the patient. The TCC transmitter module comprises a power source configured to deliver current having the amplitude to the plurality of electrodes, polarity switching circuitry coupled to the power source, wherein the polarity switching circuitry is configured to switch the polarity of the current at the frequency, and protection circuitry coupled between the power source and the plurality of electrodes, wherein the protection circuitry is configured to protect the TCC transmitter module and other circuitry within the housing of the ICD from an anti-tachyarrhythmia shock delivered to the patient by the shock module or an external device.

Figure 6A:
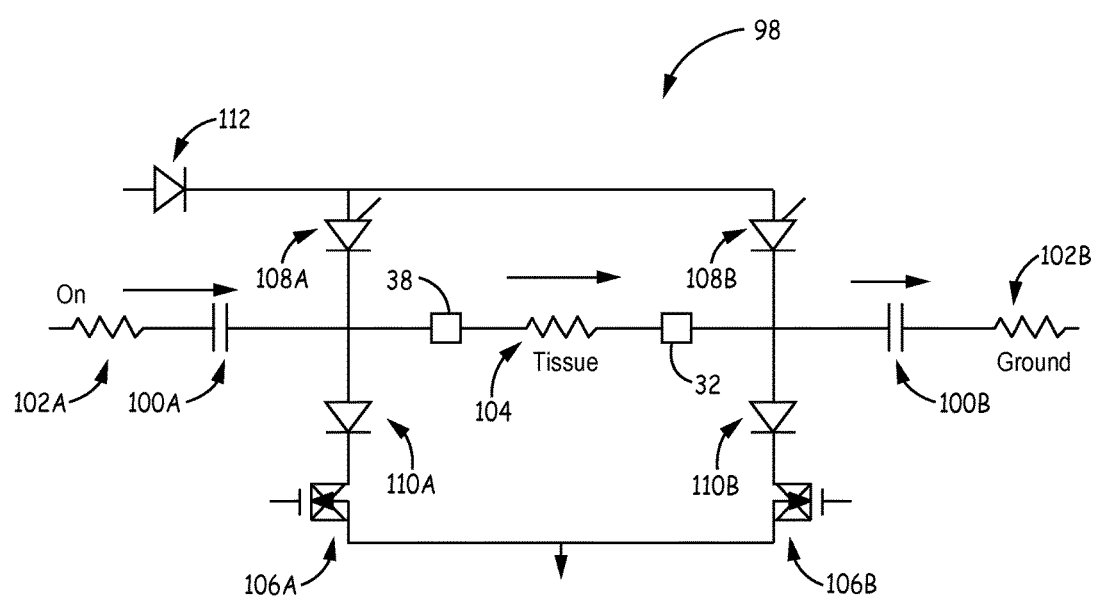
FIGS. 6A and 6B are circuit diagrams illustrating circuitry of a signal generator that includes the TCC transmitter module of FIG. 5, according to one example configuration.
Figure 6B:
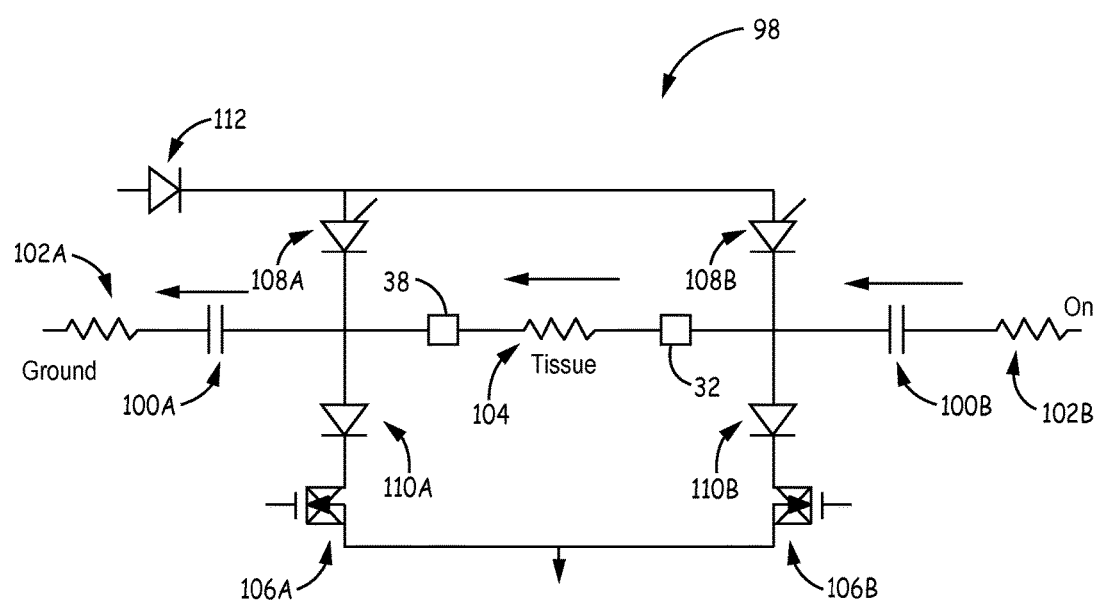

FIGS. 6A and 6B are circuit diagrams illustrating circuitry 98 of signal generator 76 according to one example configuration. Circuitry 98 illustrates one example configuration and operation of TCC transmitter module 82 in which the TCC signal is capacitively coupled to electrodes 32, 38. As illustrated in FIGS. 6A and 6B, the TCC transmitter module includes capacitors 100A and 100B respectively coupled to electrodes 32, 38. Capacitors 100A and 100B may be components of protection circuitry 96. Capacitors 100A and 100B capacitively couple a TCC signal across tissue 104 of the patient via electrodes 32, 38, while preventing a DC voltage from building up on electrodes 32, 38.

Resistors 102A and 102B are respectively connected to capacitors 100A and 100B. Resistors 102A and 102B may be components of protection circuitry 96. Resistors 102A and 102B may prevent high voltages that may develop on electrodes 32, 38, e.g., during external defibrillation, from reaching the rest of the circuitry of the ICD, including the rest of TCC transmitter module 82.

FIGS. 6A and 6B respectively illustrate different phases of the alternating TCC signal. FIGS. 6A and 6B do not illustrate components of current source 92 or polarity switching circuitry 94. However, FIGS. 6A and 6B do illustrate other components of signal generator 76, e.g., other components of shock module 78 and/or induction module 80, such as transistors 106A and 106B, which may be field effect transistors (FETs), such as high-voltage FETs, switches 108A and 108B, which may be high voltage switches, and diodes 110A, 110B, and 112. For example, transistors 106A and 106B may be components of induction module 80. In such examples, the on-off states of transistors 106A and 106B may be alternated to produce an alternating fibrillation induction waveform, e.g., having a frequency of 50 Hz, for delivery to patient 14 via electrodes 32 and 38.

In the example illustrated by FIGS. 6A and 6B, TCC transmitter module 82 does not use components of shock module 78 and/or induction module 80 for generation of the TCC signal. For example, the TCC transmitter module does not use transistors 106A and 106B, which may be kept in the off state during generation of a TCC signal, as indicated by the X's in FIGS. 6A and 6B. The different directions of TCC signal current flow through the circuit during the different phases of the alternating TCC signal is illustrated by the directional arrows in FIG. 6A and FIG. 6B.

Figure 7:
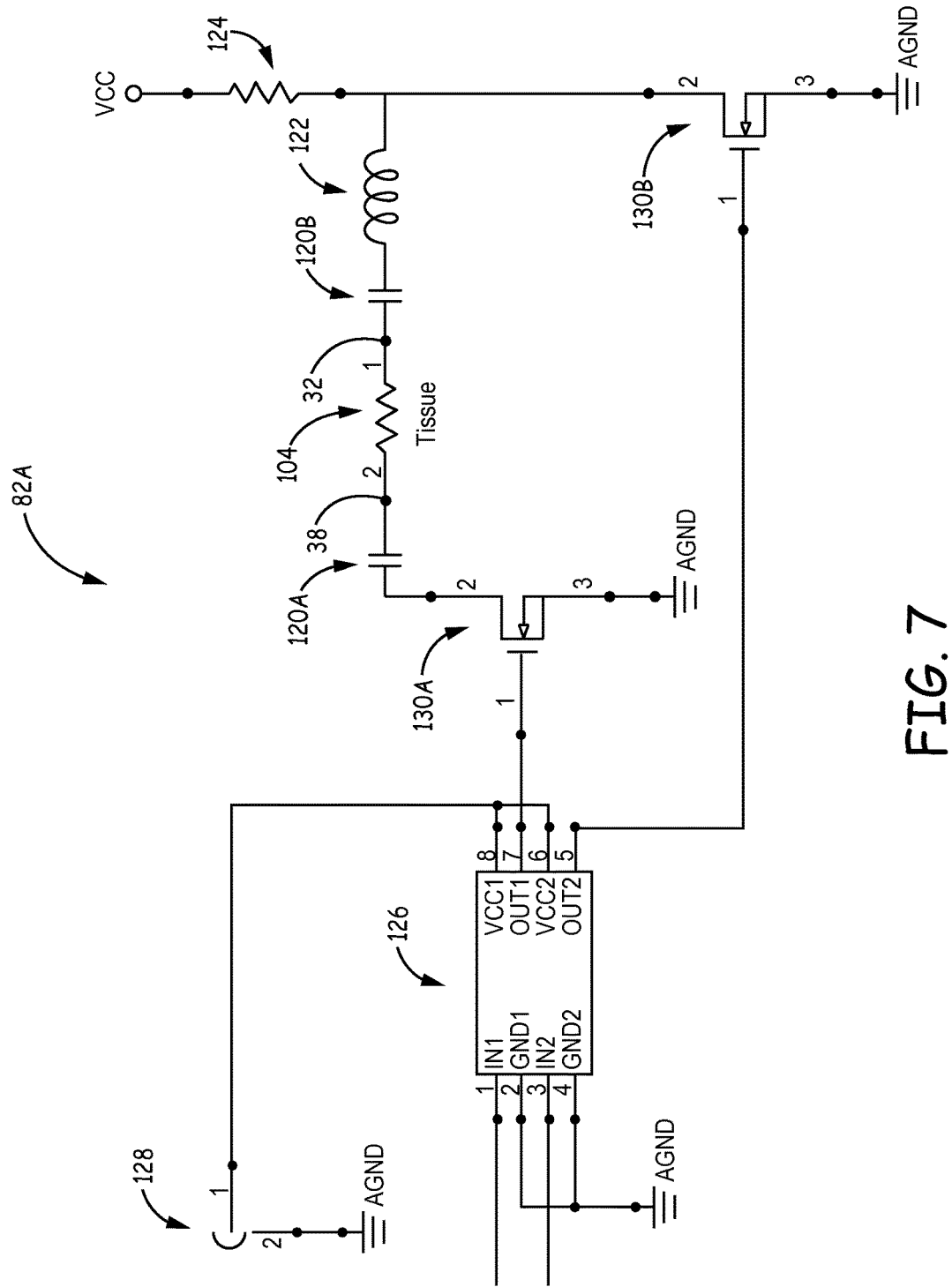
FIG. 7 is a circuit diagram illustrating an example configuration of a TCC transmitter module in which the TCC signal is capacitively coupled to the electrodes and which includes one or more LC circuits.

FIG. 7 is a circuit diagram illustrating an example configuration of a TCC transmitter module 82A in which the TCC signal is capacitively coupled to electrodes 32, 38, and which includes one or more LC circuits. The configuration of TCC transmitter module 82A illustrated in FIG. 7 may be one example implementation of TCC transmitter module 82 (FIGS. 4 and 5). TCC transmitter module 82A includes capacitors 120A and 120B, respectively coupled to electrodes 38 and 32, to capacitively couple the TCC signal to the electrodes for delivery to tissue 104 of patient 14. TCC transmitter module 82A also includes an inductor 122 coupled to capacitor 120B to form an LC circuit. The LC circuit of inductor 122 coupled to capacitor 120B, as well as capacitor 120A, may be considered components of protection circuitry 96 of TCC transmitter module 82A. Protection circuitry 96 of the example TCC transmitter module 82A of FIG. 7 also includes a resistor 124 coupled to inductor 122, which may form an RLC circuit with capacitor 120B and inductor 122.

VCC may act as the voltage supply for power source 92 of example TCC transmitter module 82A illustrated by FIG. 7. The amplitude of the current through tissue 104 may be controlled by VCC. A level shifter circuit 126 oppositely alternates the on-off states of transistors 130A and 130B at the frequency of the TCC signal by oppositely alternating the application of a voltage derived from voltage input 128, which may be the same as or different than VCC, to the gates of the transistors. Level shifter 126 and transistors 130A and 130B, which may be field effect transistors (FETs) in one example, are components of polarity switching circuitry 94 of the illustrated example TCC transmitter module 82A.

An example capacitance for capacitors 120A and 120B is 7 nanofarad (nF). An example inductance for inductor 122 is 330 microhenry (µH). An example resistance for resistor 124 is 300 ohms. However, other capacitor, inductor and resistor values may be used in other example implementations.

For purposes of testing the example TCC transmitter module 82A of FIG. 7, a TCC input signal was modulated using a high-speed digital input/output card in a computer, and applied to the inputs IN1 and IN2 of level shifter circuit 126. In an ICD, the TCC input signal to level shifter 126 may be provided by a controller of signal generator 76 and/or RF telemetry module 86, as described herein. Testing of TCC transmitter module 82A demonstrated that the circuit could generate signals having frequencies up to at least 200 kHz, e.g., transistors 130A and 130B could be switched at such frequencies, and with amplitudes within a range approximately 5 mA to approximately 40 mA.

FIGS. 8-11 are circuit diagrams illustrating other example configurations of TCC transmitter modules 82B-82E, respectively, in which the TCC signal is capacitively coupled to electrodes 32, 38, and which include one or more LC circuits. The configuration of TCC transmitter modules 82B-82E illustrated in FIGS. 8-11 are example implementations of TCC transmitter module 82 (FIGS. 4 and 5).

In each of TCC transmitter modules 82B-82E illustrated by FIGS. 8-11, electrodes 38 and 32 are coupled to a respective one of capacitors C1 and C2, which may be components of protection circuitry 96 of TCC transmitter modules 82B-82E. Additionally, each of TCC transmitter modules 82B-82E includes a voltage source V2, which may act as a component of power source 92 of the TCC transmitter module, and transistors M1 and M2, which may be FETs, such as high-voltage FETs. Level shifter A1 controls the on-off states of transistors M1 and M2 to be oppositely alternated at the frequency of the TCC signal. Oppositely alternating the on-off states of transistors M1 and M2 at the frequency of the TCC signal causes the direction of current produced by V2 through electrodes 32, 38 and tissue R4 to alternate at the frequency of the TCC signal. Level shifter A1 and transistors M1 and M2 may be considered components of polarity switching circuitry 94 of TCC transmitter modules 82B-82E.

Figure 8:
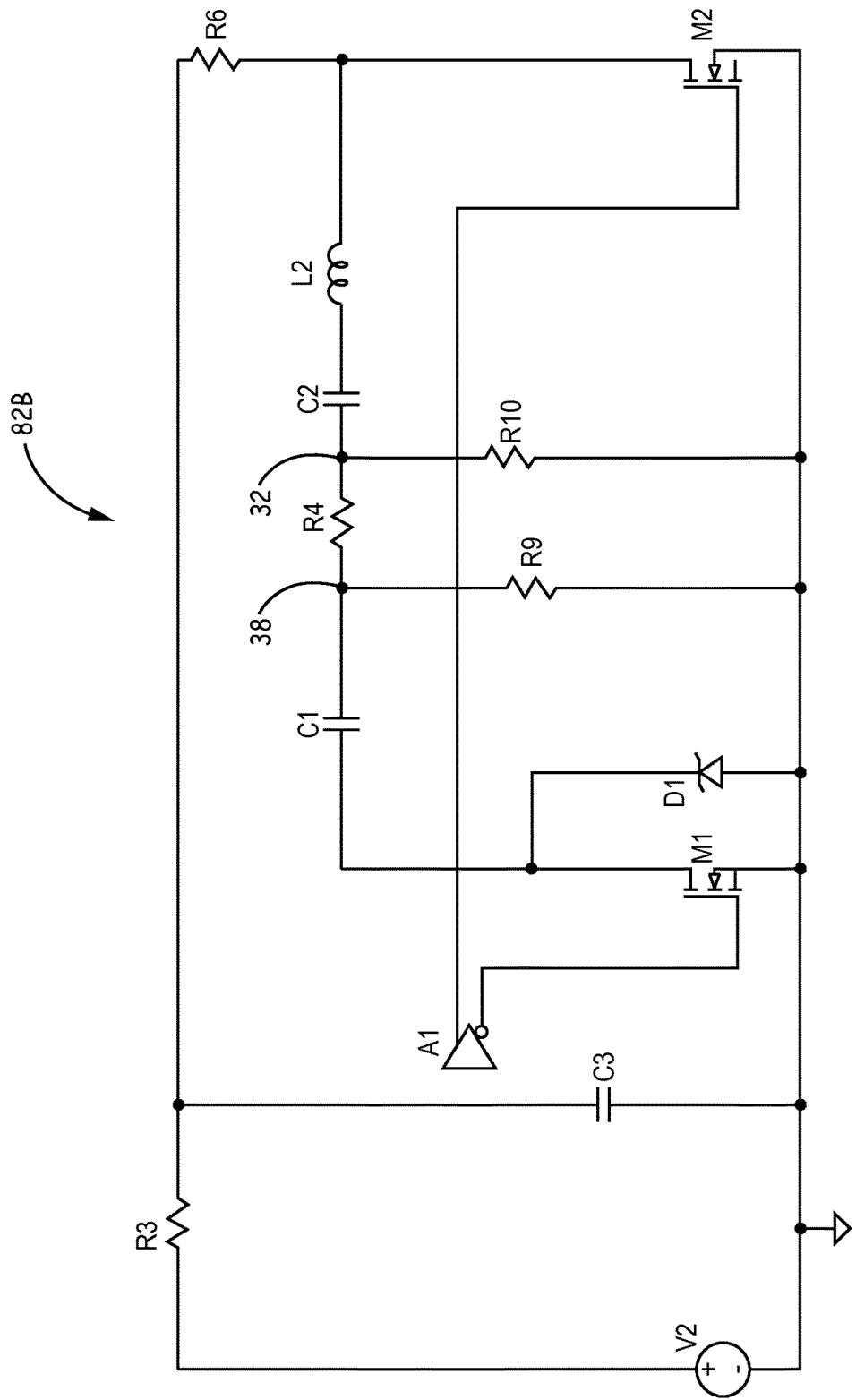
FIGS. 8-11 are circuit diagrams illustrating other example configurations of TCC transmitter modules in which the TCC signal is capacitively coupled to the electrodes and which include one or more LC circuits.

Example TCC transmitter module 82B illustrated by FIG. 8 includes an inductor L2 connected to capacitor C2. Inductor L2 and capacitor C2 may form an LC circuit that is part of protection circuitry 96 of TCC transmitter module 82B. As discussed herein, the pass-band of the LC circuit may be configured such that the LC circuit passes TCC signals. TCC transmitter module 82B, as illustrated by FIG. 8, also includes resistor R6 connected parallel with inductor L2 and capacitor C2. The combination of resistor R6, inductor L2, and capacitor C2 may form an RLC circuit that is part of protection circuitry 96 of the TCC transmitter module. Resistors R9 and R10 may also be considered components of protection circuitry 96. TCC transmitter module 82B also includes diode D1, which may be a Zener diode, coupled in parallel with transistor M1 to protect the transistor.

An example capacitance value for C1 and C2 in the example of FIG. 8 is 3 nF. An example inductance value of inductor L2 in the example of FIG. 8 is 680 µH. Example resistance values of resistors R3, R4 (tissue), R6, R9, and R10 in the example of FIG. 8 are 75 ohm, 50 ohm, 300 ohm, 250,000 ohm, and 250,000 ohm, respectively. An example voltage for voltage source V2 in the example of FIG. 8 is 7 volts. However, other capacitor, inductor, resistor, and voltage values may be used in other example implementations.

Figure 9:
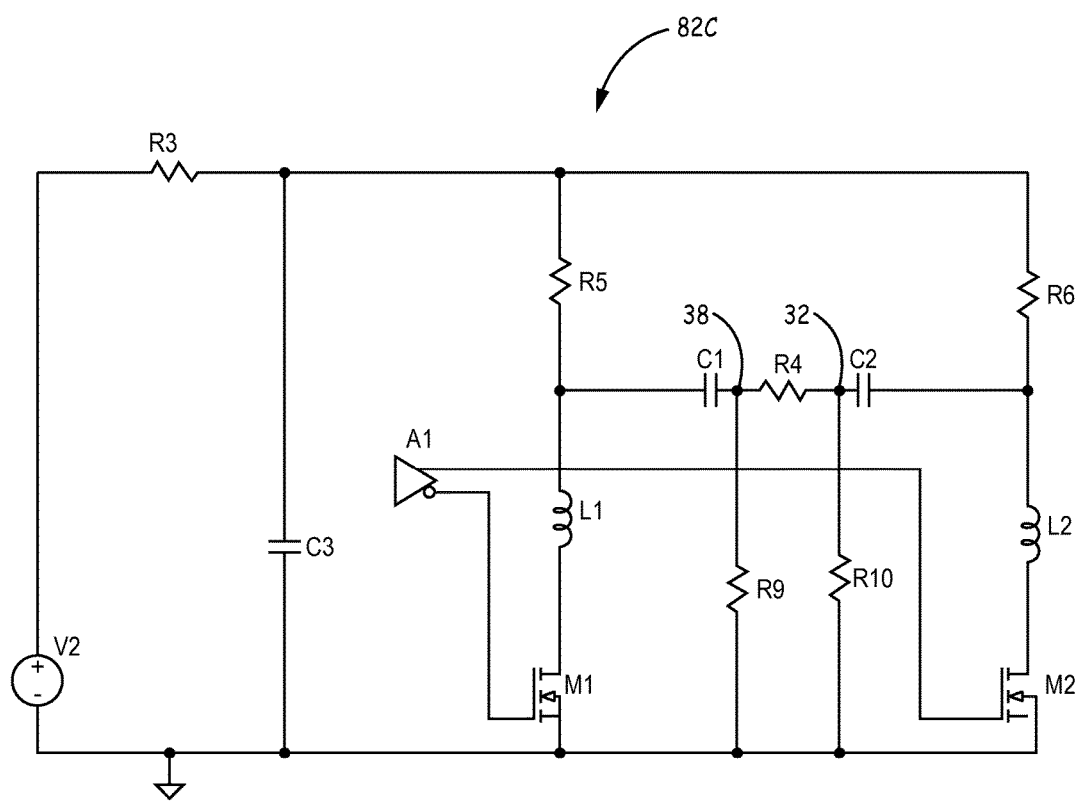

TCC transmitter module 82C of FIG. 9 includes inductors L1 and L2 respectively connected to capacitors C1 and C2 to form LC circuits that may be considered part of protection circuitry 96 of TCC transmitter module 82C. TCC transmitter module 82C of FIG. 9 also includes resistors R5 and R6 coupled in parallel with inductor L1 and capacitor C1, and inductor L2 and capacitor C2, respectively. Respective RLC circuits, which may be considered part of protection circuitry 96 of TCC transmitter module 82C, may be formed by the combinations of: resistor R5, inductor L1, and capacitor C1; and resistor R6, inductor L2, and capacitor C2. Relative to TCC transmitter module 82B of FIG. 8, the addition of inductor L1 and resistor R5 in TCC transmitter module 82C of FIG. 9 may provide greater protection of the circuitry of the ICD from voltages across electrodes 32, 38. However, the addition of inductor L1 and resistor R5 in TCC transmitter module 82C of FIG. 9 may increase the component count and current consumption relative to the example circuitry of TCC transmitter module 82B of FIG. 8. Relative to TCC transmitter module 82B of FIG. 8, TCC transmitter module 82C of FIG. 9 also does not include protection diode D1 coupled in parallel to transistor M1.

An example capacitance value for C1 and C2 in the example of FIG. 9 is 1.45 nF. An example inductance value of inductors L1 and L2 in the example of FIG. 9 is 680 µH. Example resistance values of resistors R3, R4 (tissue), R5, R6, R9 and R10 in the example of FIG. 9 are 75 ohm, 50 ohm, 570 ohm, 570 ohm, 250,000 ohm, and 250,000 ohm, respectively. An example voltage for voltage source V2 in the example of FIG. 9 is 7 volts. However, other capacitor, inductor, resistor, and voltage values may be used in other example implementations.

Figure 10:
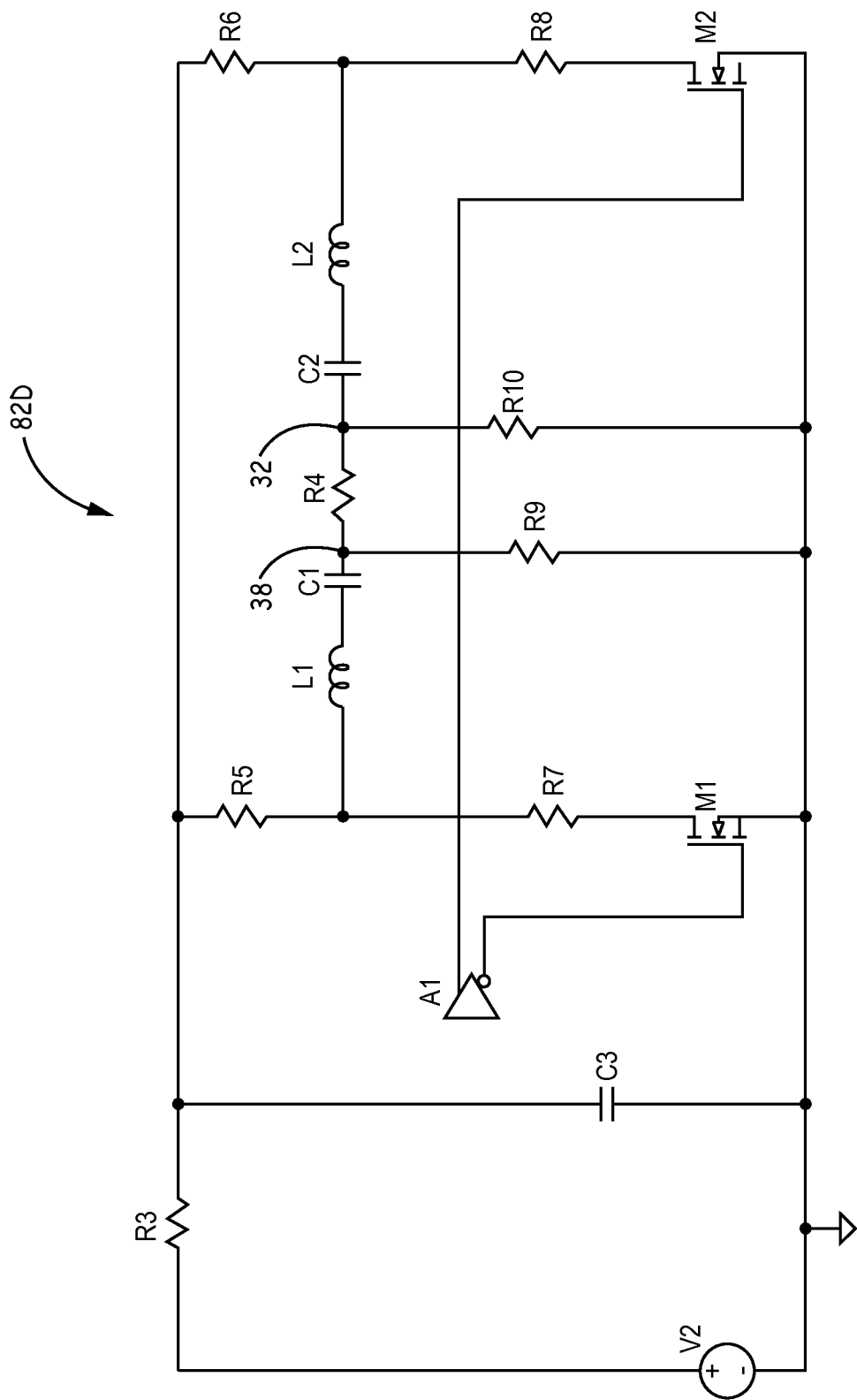

Relative to example TCC transmitter module 82C of FIG. 9, example TCC transmitter module 82D of FIG. 10 includes additional resistors R7 and R8 connected in series between inductor L1 and transistor M1, and between inductor L2 and transistor M2, respectively. Resistors R7 and R8 may, when combined with inductor L1 and capacitor C1, and inductor L2 and capacitor C2, respectively, form respective RLC circuits that may be part of protection circuitry 96 of TCC transmitter module 82D. Resistors R7 and R8 may each have a resistance of approximately 150 ohm. However, other resistor values may be used in other example implementations.

Figure 11:
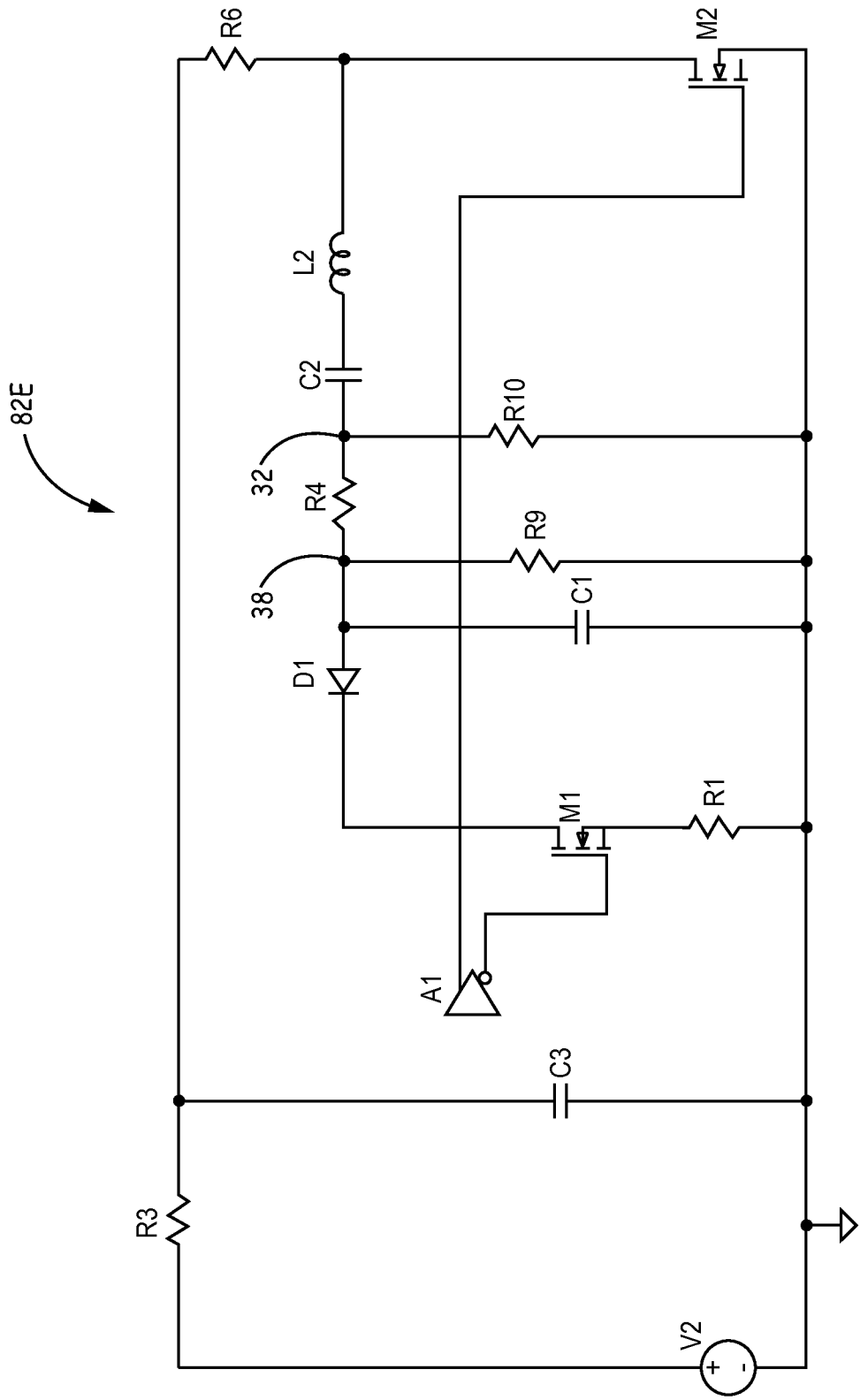

The example TCC transmitter module 82E of FIG. 11 is similar to TCC transmitter module 82B of FIG. 8, except that transistor M1 may be a component of signal generator 76 used for other purposes, such as to generate a signal for lead impedance measurements, which may reduce the number of components within signal generator 76 relative to examples in which a transistor is added to for the TCC transmitter module. Transistor M1 is connected to a resistor R1, which may have a resistance within a range from approximately 10 ohm to approximately 50 ohm, such as approximately 30 ohm, and diode D1, which controls current flow through the circuit, e.g., depending on whether transistor M1 is used for generation of TCC or lead impedance signals. Additionally, in TCC transmitter module 82E, capacitor C1 is connected in parallel with diode D1, shared transistor M1 and resistor R1, rather than in series with the dedicated transistor of TCC transmitter module 82B of FIG. 8. An example voltage value for source V2 in the example TCC transmitter module 82E of FIG. 11 is 5 volts. However, other resistor and voltage values may be used in other example implementations.

In an alternative to example TCC transmitter module 82E of FIG. 11, a Zener diode is added, e.g., in parallel, to protect transistor M2. However, simulation of this alternative indicated that the voltage on capacitor C2 could exceed 2300 volts during defibrillation. In some examples, transistor M2 may be configured as a high voltage transistor without Zener protection.

Figure 12:
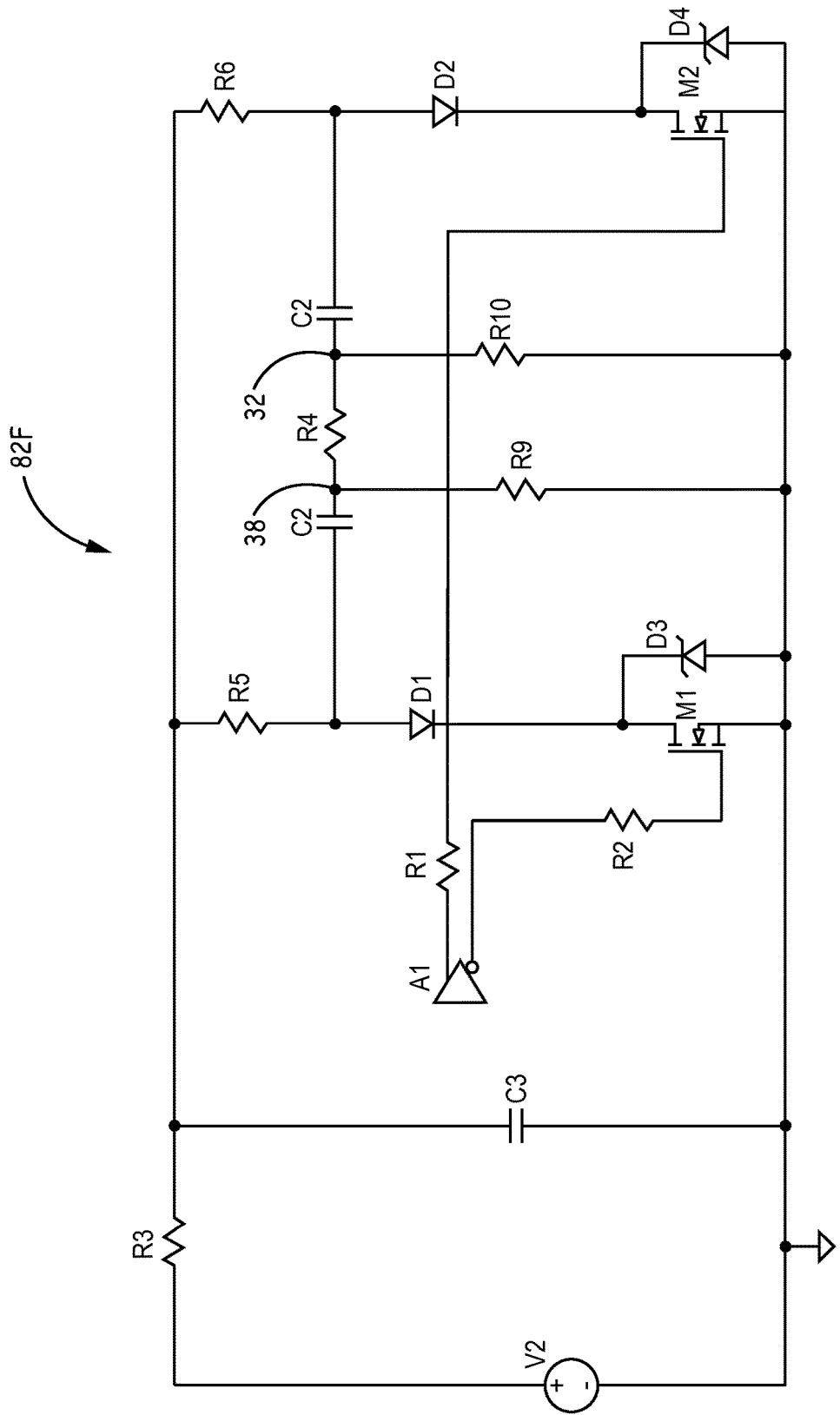
FIG. 12 is a circuit diagram illustrating another example configuration of a TCC transmitter module in which the TCC signal is capacitively coupled to the electrodes.

FIG. 12 is a circuit diagram illustrating another example configuration of a TCC transmitter module 82F in which the TCC signal is capacitively coupled to electrodes 32, 38. TCC transmitter module 82F may be another example implementation of TCC transmitter module 82 of FIGS. 4 and 5. However, unlike the examples of FIGS. 8-11, TCC transmitter module 82F of FIG. 12 does not include an inductor coupled to either of capacitors C1 or C2. Instead, protection circuitry 96 of TCC transmitter module 82F includes diodes D1 and D2, and resistors R1, R2, R5, and R6 to protect the ICD circuitry, including TCC transmitter module 82F, from voltages across electrodes 32, 38.

An example capacitance value for C1 and C2 in the example of FIG. 12 is 47 nF. Example resistance values of resistors R1, R2, R3, R4 (tissue), R5, R6, R9 and R10 in the example of FIG. 12 are 250 ohm, 250 ohm, 75 ohm, 50 ohm, 700 ohm, 700 ohm, 250,000 ohm, and 250,000 ohm, respectively. An example voltage for voltage source V2 in the example of FIG. 12 is 8.2 volts. However, other capacitor, inductor, resistor, and voltage values may be used in other example implementations.

Figure 13A:
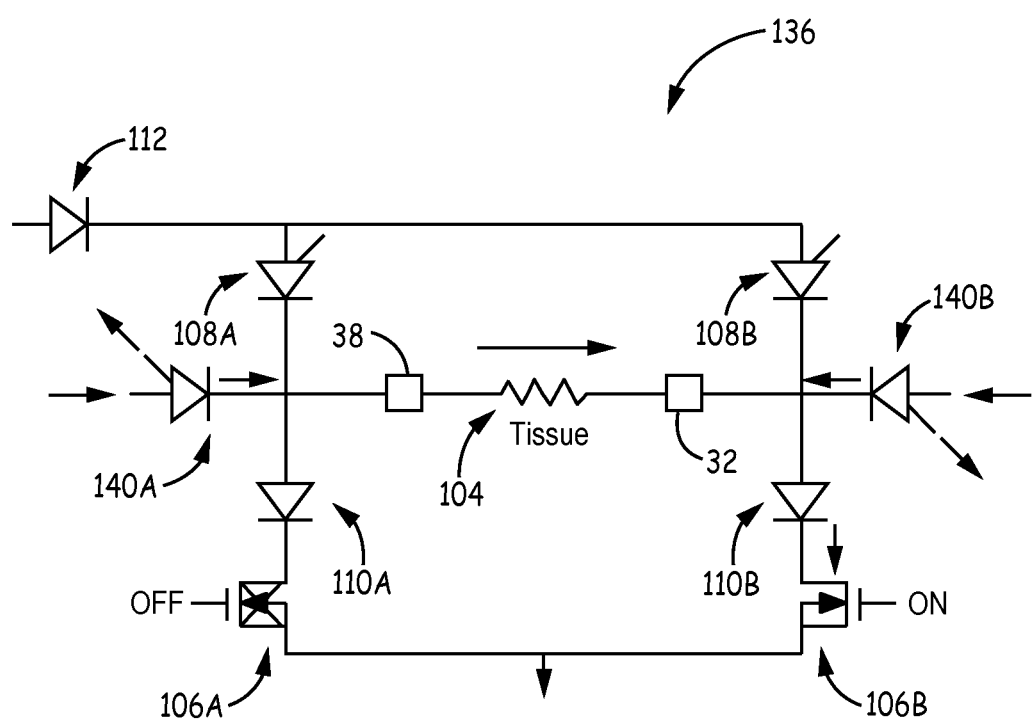
FIGS. 13A and 13B are circuit diagrams illustrating circuitry of a signal generator that includes another example configuration the TCC transmitter module of FIG. 5.
Figure 13B:
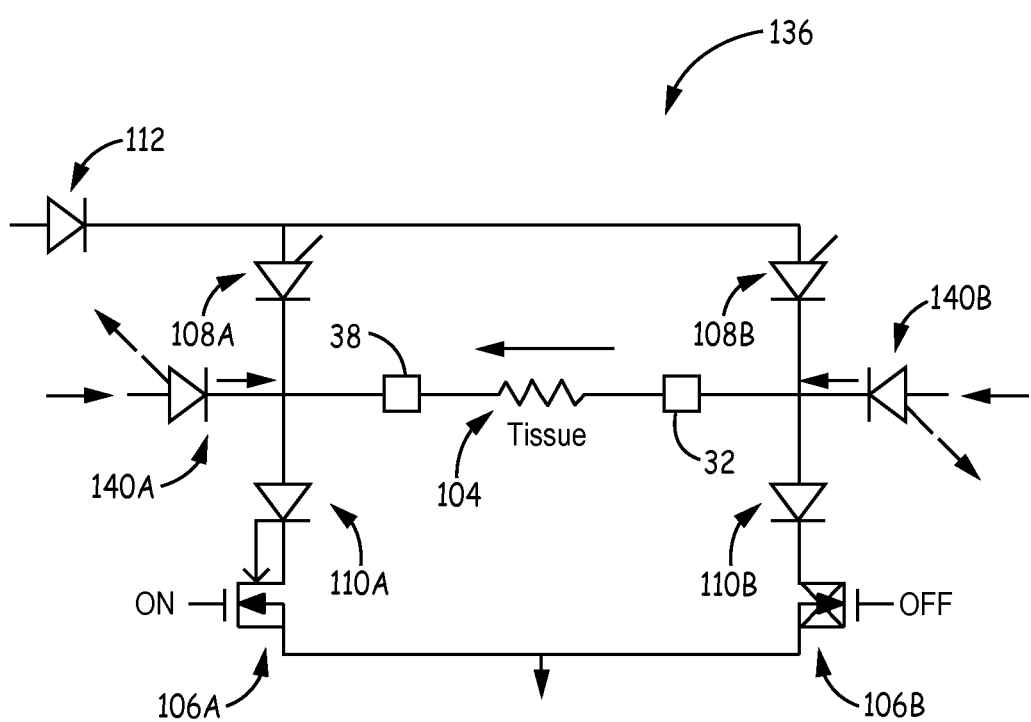

FIGS. 13A and 13B are circuit diagrams illustrating circuitry 136 of signal generator 76 according to another example configuration. Circuitry 136 illustrates one example configuration and operation of TCC transmitter module 82 in which the TCC signal is coupled to electrodes 32, 38 by high-voltage switches. Like the example circuitry 98 of FIGS. 6A and 6B, the circuitry 136 of FIGS. 13A and 13B includes electrodes 32 and 38 coupled to tissue 104, transistors 106A and 106B, switches 108A and 108B, and diodes 110A, 110B, and 112. However, the example circuitry 136 of FIGS. 13A and 13B does not include capacitors and one or more inductors, and instead includes high-voltage switches 140A and 140B coupled to electrode 38 and electrode 32, respectively. Switches 140A and 140B may be considered components of both protection circuitry 96 and power source 92 of TCC transmitter module 82 according to this example configuration. For example, high voltage switches 140A and 140B may protect the circuitry of the ICD from high voltages on electrodes 32, 38. Switches 140A and 140B may also both be placed in an on state during generation of a TCC signal to source the TCC signal current for application to electrodes 32, 38. For example, switches 140A and 140B may be placed in an on state by applying approximately 50 mA to the anode and sinking approximately 40 mA from the gate, which may keep the switch on, and which may result is a constant approximately 10 mA from each cathode.

FIGS. 13A and 13B illustrate how a biphasic waveform would be generated through the tissue using the switching transistors 106A and 106B. In general, the directional arrows in FIGS. 13A and 13B illustrate the direction of current flow in circuitry 136 during the different phases of the TCC signal. Transistors 106A and 106B may be FETs, such as high-voltage FETS. With transistor 106A off (as illustrated by the X) and transistor 106B on, as illustrated in FIG. 13A, the current that flows out of the cathode of switch 140A flows through tissue from electrode 38 to electrode 32. The current that flows through the tissues combines with the current that flows out of the cathode of switch 106B and the combined current flows to ground through switching transistor 106B. With transistor 106A on and transistor 106B off (as illustrated by the X), as illustrated in FIG. 13B, the current that flows out of the cathode of switch 140B flows through tissue in the opposite direction, from electrode 32 to electrode 38, as illustrated by the directional arrow. By oppositely alternating the on-off states of transistors 106A and 106B, the TCC signal may be alternated at the desired frequency for the TCC signal. The on-off states of transistors 106A and 106B may be controlled in the manner described above with respect to FIGS. 7-12.

In some examples, transistors 106A and 106B may be components of signal generator 76 that are additionally used for other purposes. For example, transistors 106A and 106B may be components of induction module 80. In such examples, the on-off states of transistors 106A and 106B may be alternated to produce an alternating fibrillation induction waveform, e.g., having a frequency of 50 Hz, for delivery to patient 14 via electrodes 32 and 38. Using transistors 106A and 106B for both TCC and fibrillation induction signal generation may reduce the component count and power consumption of signal generator 76 relative to examples with dedicated transistors for TCC signal generation.

Figure 14A:
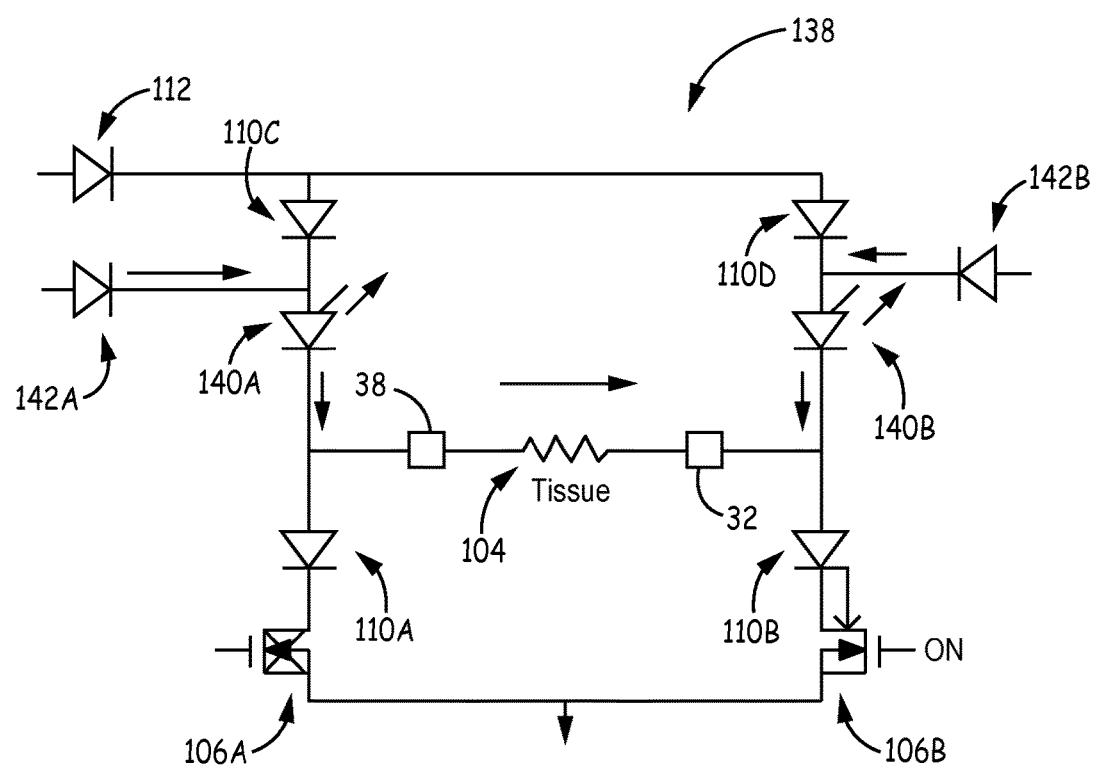
FIGS. 14A and 14B are circuit diagrams illustrating circuitry of a signal generator that includes another example configuration of the TCC transmitter module of FIG. 5.
Figure 14B:
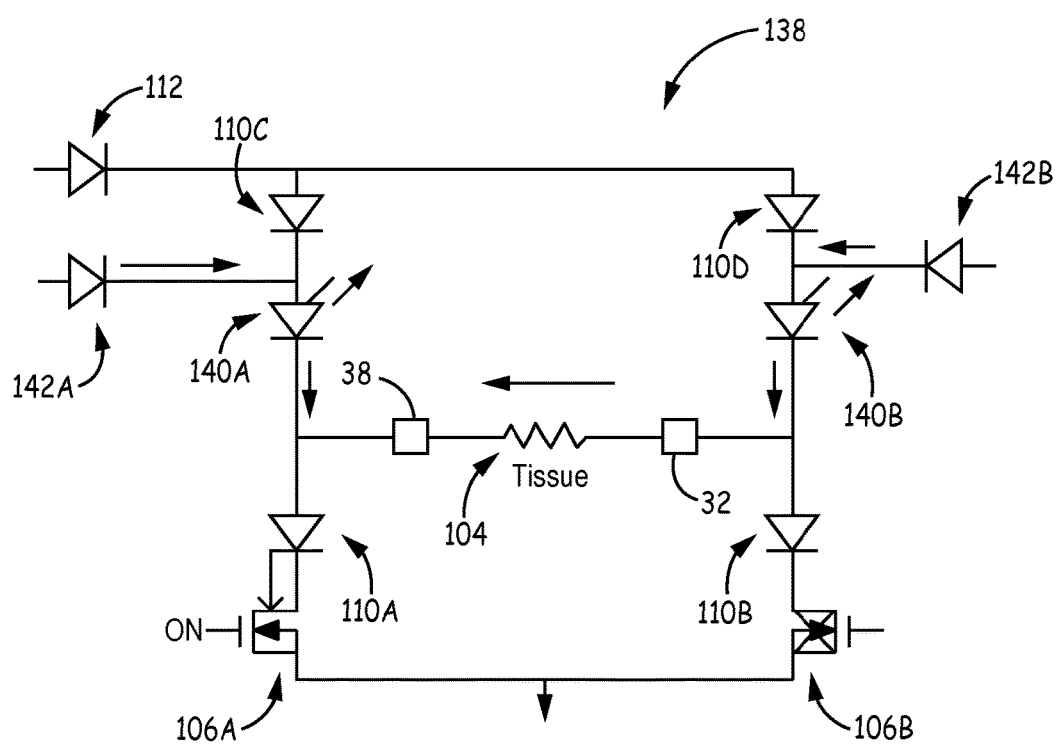

FIGS. 14A and 14B are circuit diagrams illustrating circuitry 138 of signal generator 76 according to another example configuration. Circuitry 138 illustrates another example configuration and operation of TCC transmitter module 82 in which the TCC signal is coupled to electrodes 32, 38 by high-voltage switches. The example circuitry 138 of FIGS. 14A and 14B is substantially similar to circuitry 136 of FIGS. 13A and 13B, except that circuitry 138 includes diodes 142A and 142B, though which current is delivered to switches 140A and 140B, as well as additional diodes 110C and 110D. Diodes 142A, 142B, 110C, and 110D may act as protection circuitry 96 of TCC transmitter module 82 by blocking current flow around the example circuit.

Figure 15:
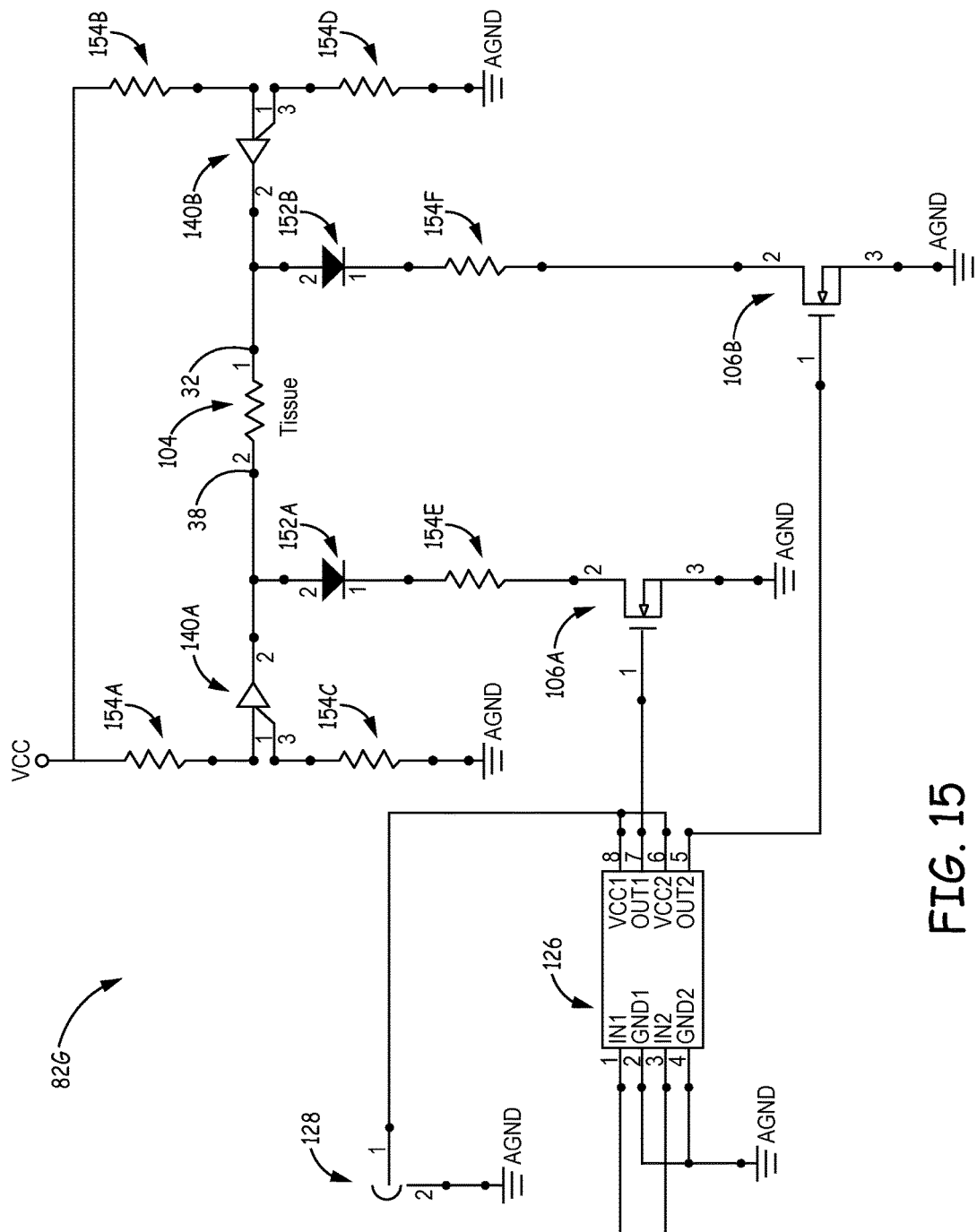
FIG. 15 is a circuit diagram an example configuration of a TCC transmitter module in which the TCC signal is delivered to the electrodes by high-voltage switches.

FIG. 15 is a circuit diagram an example configuration of a TCC transmitter module 82G in which the TCC signal is delivered to electrodes 32, 38 by high-voltage switches. TCC transmitter module 82G may be one example implementation of TCC transmitter module 82 of FIGS. 4 and 5. Like TCC transmitter module 82A of FIG. 7, the TCC transmitter module 82G of FIG. 15 includes a voltage source VCC, level shifter circuit 126, and a voltage source 128. However, rather than transistors 130A and 130B, TCC transmitter module 82G includes transistors 106A and 106B from induction module 80. Additionally, rather than capacitors and one or more inductors, TCC transmitter module 82G includes switches 140A and 140B connected to electrode 38 and electrode 32, respectively. TCC transmitter module 82G also includes diodes 152A and 152B, which may be components of protection circuitry 96 of TCC transmitter module 82G, as well as resistors 154A-154F. Resistors 154A-154D may bias switches 140A and 140B on to produce the current of the TCC signal through tissue 104. An example resistance value for resistors 154A and 154B is 15 ohms, and an example resistance value for resistors 154C and 154D is 25 ohms. Resistors 154E and 154F may have a value of 90 ohms, for example.

FIGS. 6A-15 illustrate example circuitry of a number of example implementations of TCC transmitter module 82 of FIGS. 4 and 5, which may include current source 92, polarity switching circuitry 94, and protection circuitry 96. For example, TCC transmitter modules 82A-82G of FIGS. 7-12 and 15 may be example implementations of TCC transmitter module 82 of FIGS. 4 and 5, which may include power source 92, polarity switching circuitry 94, and protection circuitry 96. However, other example implementations TCC transmitter module 82, including different circuit components, or different arrangements or values of the illustrated components, are contemplated.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to ICD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between ICD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for generating and delivering a TCC signal by an ICD. Any combination of the described operations or functions is contemplated. These and other examples are within the scope of the following claims.

What is claimed is:

1. An implantable cardioverter defibrillator (ICD) configured to transmit a tissue conduction communication (TCC) signal, the ICD comprising:
    a housing;
    a plurality of electrodes; and
    a signal generator within the housing, the signal generator comprising:
        a shock module coupled to the plurality of electrodes, wherein the shock module is configured to generate an anti-tachyarrhythmia shock and deliver the anti-tachyarrhythmia shock to a patient via the plurality of electrodes; and
        a TCC transmitter module coupled to the plurality of electrodes, wherein the TCC transmitter module is configured to generate the TCC signal and transmit the TCC signal via the plurality of electrodes, wherein the TCC signal comprises a biphasic signal having an amplitude and a frequency, wherein at least one of the amplitude or the frequency is configured to avoid stimulation of tissue of the patient by the TCC signal, and wherein the TCC transmitter module comprises:
            a power source configured to deliver current having the amplitude to the plurality of electrodes;
            polarity switching circuitry coupled to the power source, wherein the polarity switching circuitry is configured to switch the polarity of the current at the frequency; and
            protection circuitry coupled between the power source and the plurality of electrodes, wherein the protection circuitry is configured to protect the TCC transmitter module and other circuitry within the housing of the ICD from an anti-tachyarrhythmia shock delivered to the patient by the shock module or an external device, and a standoff voltage of the protection circuitry is greater than 2000 volts (V).

2. The ICD of claim 1, wherein the frequency is at least 100 kilohertz (kHz).

3. The ICD of claim 1, wherein the frequency is within a range from 150 kilohertz (kHz) to 200 kHz.

4. The ICD of claim 3, wherein the polarity switching circuitry is configured to toggle the frequency between 150 kHz and 200 kHz.

5. The ICD of claim 1, wherein the amplitude is within a range from 5 milliamps (mA) to 40 mA.

6. The ICD of claim 1, wherein the amplitude is within a range from 5 milliamps (mA) 10 mA.

7. The ICD of claim 1, wherein the protection circuitry comprises:
    a first capacitor coupled between the power source and a first electrode of the plurality of electrodes; and
    a second capacitor coupled between the power source and a second electrode of the plurality of electrodes.

8. The ICD of claim 7, wherein the protection circuitry comprises a first LC circuit that comprises the first capacitor and a first inductor.

9. The ICD of claim 8, wherein the protection circuitry comprises a second LC circuit that comprises the second capacitor and a second inductor.

10. The ICD of claim 8, wherein the frequency of the TCC signal is within a pass-band of the first LC circuit.

11. The ICD of claim 10, wherein the pass-band is within a range from 150 kilohertz (kHz) to 200 kHz.

12. The ICD of claim 1, wherein the housing comprises a first electrode of the plurality of electrodes, and a coil electrode coupled to the ICD by a lead comprises a second electrode of the plurality of electrodes.

13. The ICD of claim 1, further comprising:
    an antenna; and
    a radio-frequency (RF) telemetry module configured to transmit and receive RF telemetry signals via the antenna,
    wherein the RF telemetry module is further configured to modulate the TCC signal, and at least one of the power source or the polarity switching circuitry of the TCC transmitter module generates the TCC signal according to the modulation.

14. The ICD of claim 1, wherein the ICD comprises an extravascular ICD, and the plurality of electrodes are configured for extravascular implantation.

15. An implantable cardioverter defibrillator (ICD) configured to transmit a tissue conduction communication (TCC) signal, the ICD comprising:
a housing;
a plurality of electrodes; and
a signal generator within the housing, the signal generator comprising:
  a shock module coupled to the plurality of electrodes, wherein the shock module is configured to generate an anti-tachyarrhythmia shock and deliver the anti-tachyarrhythmia shock to a patient via the plurality of electrodes; and
  a TCC transmitter module coupled to the plurality of electrodes, wherein the TCC transmitter module is configured to generate the TCC signal and transmit the TCC signal via the plurality of electrodes, wherein the TCC signal comprises a biphasic signal having an amplitude and a frequency, wherein at least one of the amplitude or the frequency is configured to avoid stimulation of tissue of the patient by the TCC signal, and wherein the TCC transmitter module comprises:
    a power source configured to deliver current having the amplitude to the plurality of electrodes;
    polarity switching circuitry coupled to the power source, wherein the polarity switching circuitry is configured to switch the polarity of the current at the frequency; and
    protection circuitry coupled between the power source and the plurality of electrodes, wherein the protection circuitry is configured to protect the TCC transmitter module and other circuitry within the housing of the ICD from an anti-tachyarrhythmia shock delivered to the patient by the shock module or an external device,
    wherein the power source and the protection circuitry comprise at least two common high-voltage switches,
    wherein a first high-voltage switch of the at least two common high-voltage switches is coupled to a first electrode of the plurality of electrodes, and a second high-voltage switch of the at least two common high-voltage switches is coupled to a second electrode of the plurality of electrodes, and
    wherein cathodes of the first and second high-voltage switches deliver current to the plurality of electrodes.

16. The ICD of claim 15, wherein a standoff voltage of the protection circuitry is greater than 2000 volts (V).

17. An implantable cardioverter defibrillator (ICD) configured to transmit a tissue conduction communication (TCC) signal, the ICD comprising:
a housing,
a plurality of electrodes, and
a signal generator within the housing, the signal generator comprising:
  a shock module coupled to the plurality of electrodes, wherein the shock module is configured to generate an anti-tachyarrhythmia shock and deliver the anti-tachyarrhythmia shock to a patient via the plurality of electrodes, and
  a TCC transmitter module coupled to the plurality of electrodes, wherein the TCC transmitter module is configured to generate the TCC signal and transmit the TCC signal via the plurality of electrodes, wherein the TCC signal comprises a biphasic signal having an amplitude and a frequency, wherein at least one of the amplitude or the frequency is configured to avoid stimulation of tissue of the patient by the TCC signal, and wherein the TCC transmitter module comprises:
    a power source configured to deliver current having the amplitude to the plurality of electrodes,
    polarity switching circuitry coupled to the power source, wherein the polarity switching circuitry is configured to switch the polarity of the current at the frequency, wherein the polarity switching circuitry comprises:
      a first transistor coupled to a first electrode of the plurality of electrodes; and
      a second transistor coupled to a second electrode of the plurality of electrodes, and
      wherein on-off states of the first and second transistors are oppositely alternated at the frequency to switch the polarity of the current at the frequency; and
    protection circuitry coupled between the power source and the plurality of electrodes, wherein the protection circuitry is configured to protect the TCC transmitter module and other circuitry within the housing of the ICD from an anti-tachyarrhythmia shock delivered to the patient by the shock module or an external device.

18. The ICD of claim 17, wherein the first and second transistors are included in a fibrillation induction module configured to generate a fibrillation induction signal, wherein the fibrillation induction signal is configured to induce fibrillation of a heart of the patient.

19. The ICD of claim 17, wherein a standoff voltage of the protection circuitry is greater than 2000 volts (V).

20. An extravascular implantable cardioverter defibrillator (ICD) configured to transmit a tissue conduction communication (TCC) signal, the extravascular ICD comprising:
a housing configured for extravascular implantation within a patient, wherein the housing comprises a housing electrode; and
a signal generator within the housing, the signal generator comprising:
  a shock module coupled to the housing electrode and a coil electrode, wherein the coil electrode is configured for extravascular implantation within the patient and is coupled to the extravascular ICD by an implantable lead, wherein the shock module is configured to generate an anti-tachyarrhythmia shock and deliver the anti-tachyarrhythmia shock to a patient via the housing electrode and the coil electrode; and
  a TCC transmitter module coupled to the housing electrode and the coil electrode, wherein the TCC transmitter module is configured to generate the TCC signal and transmit the TCC signal via the housing electrode and the coil electrode, wherein the TCC signal comprises a biphasic signal having an amplitude and a frequency, wherein at least one of the amplitude or the frequency is configured to avoid stimulation of tissue of the patient by the TCC signal, wherein the frequency is at least 100 kHz and the amplitude is within a range from 5 mA to 40 mA, and wherein the TCC transmitter module comprises:

a power source configured to deliver a current having the amplitude to the electrodes;

polarity switching circuitry coupled to the power source, the polarity switching circuitry configured to switch the polarity of the current at the frequency; and protection circuitry coupled between the power source and the electrodes, wherein the protection circuitry is configured to protect the TCC transmitter module and other circuitry within the housing of the ICD from an anti-tachyarrhythmia shock delivered to the patient by the shock module or an external device, and wherein the protection circuitry comprises:

an LC circuit that comprises a first capacitor coupled between the power source and one of the electrodes and an inductor, wherein the frequency of the TCC signal is within a passband of the LC circuit; and a second capacitor coupled between the power source and the other of the electrodes.

* * * * *